US00RE48197E

(19) United States
(12) Reissued Patent
Cho et al.

(10) Patent Number: US RE48,197 E
(45) Date of Reissued Patent: Sep. 8, 2020

(54) ATRIAL CONTRACTION DETECTION BY A VENTRICULAR LEADLESS PACING DEVICE FOR ATRIO-SYNCHRONOUS VENTRICULAR PACING

(71) Applicant: Medtronic, Inc., Minneapolis, MN (US)

(72) Inventors: Yong K. Cho, Excelsior, MN (US); Aleksandre T. Sambelashvili, Maple Grove, MN (US); Todd J. Sheldon, North Oaks, MN (US)

(73) Assignee: Medtronic, Inc., Minneapolis, MN (US)

(21) Appl. No.: 16/045,277

(22) Filed: Jul. 25, 2018

Related U.S. Patent Documents

Reissue of:
(64) Patent No.: 9,399,140
Issued: Jul. 26, 2016
Appl. No.: 14/579,105
Filed: Dec. 22, 2014

U.S. Applications:
(60) Provisional application No. 62/028,957, filed on Jul. 25, 2014.

(51) Int. Cl.
*A61N 1/00* (2006.01)
*A61N 1/365* (2006.01)
(Continued)

(52) U.S. Cl.
CPC ..... *A61N 1/06* (2013.01)

(58) Field of Classification Search
CPC .... A61N 1/3765; A61N 1/365; A61N 1/3682; A61N 1/3688
(Continued)

(56) References Cited

U.S. PATENT DOCUMENTS 3,486,506 A 12/1969 Auphan
3,659,615 A 5/1972 Enger
(Continued)

FOREIGN PATENT DOCUMENTS

CN 101185789 A 5/2008
CN 101284160 A 10/2008
(Continued)

OTHER PUBLICATIONS

Delnoy, Peter Paul et al., "Validation of a peak endocardial acceleration-based algorithm to optimize cardiac resynchronization: early clinical results," *Europace*, 10:801-8, Jul. 2008.
(Continued)

*Primary Examiner* — Beverly M Flanagan
(74) *Attorney, Agent, or Firm* — Shumaker & Sieffert, P.A.

(57) ABSTRACT

A leadless pacing device (LPD) includes a motion sensor configured to generate a motion signal as a function of heart movement. The LPD is configured to analyze the motion signal within an atrial contraction detection window that begins an atrial contraction detection delay period after activation of the ventricle, and detect a contraction of an atrium of the heart based on the analysis of the motion signal within the atrial contraction detection window. If the LPD does not detect a ventricular depolarization subsequent to the atrial contraction, e.g., with an atrio-ventricular (AV) interval beginning when the atrial contraction was detected, the LPD delivers a ventricular pacing pulse.

26 Claims, 11 Drawing Sheets

(51) Int. Cl.
*A61N 1/372* (2006.01)
*A61N 1/375* (2006.01)
*A61N 1/06* (2006.01)

(58) Field of Classification Search
USPC ..... 607/9, 18, 30, 25
See application file for complete search history.

(56) References Cited

U.S. PATENT DOCUMENTS 3,678,937 A 7/1972 Cole et al.
3,693,625 A 9/1972 Auphan
3,835,864 A 9/1974 Rasor et al.
3,943,936 A 3/1976 Rasor et al.
4,091,818 A 5/1978 Brownlee et al.
4,157,720 A 6/1979 Greatbatch
RE30,366 E 8/1980 Rasor et al.
4,256,115 A 3/1981 Bilitch
4,333,469 A 6/1982 Jeffcoat et al.
5,170,784 A 12/1992 Ramon et al.
5,179,947 A 1/1993 Meyerson et al.
5,193,539 A 3/1993 Schulman et al.
5,193,540 A 3/1993 Schulman et al.
5,243,977 A 9/1993 Trabucco et al.
5,312,439 A 5/1994 Loeb
5,324,316 A 6/1994 Schulman et al.
5,404,877 A 4/1995 Nolan et al.
5,405,367 A 4/1995 Schulman et al.
5,411,535 A 5/1995 Fujii et al.
5,438,990 A 8/1995 Wahlstrand et al.
5,441,527 A 8/1995 Erickson et al.
5,496,361 A 3/1996 Moberg et al.
5,529,578 A 6/1996 Struble
5,549,650 A 8/1996 Bornzin et al.
5,674,259 A 10/1997 Gray
5,697,958 A 12/1997 Paul et al.
5,722,998 A 3/1998 Prutchi et al.
5,792,208 A 8/1998 Gray
5,814,089 A 9/1998 Stokes et al.
5,843,132 A 12/1998 Ilvento
5,891,175 A 4/1999 Walmsley et al.
5,895,414 A 4/1999 Sanchez-Zambrano
5,954,757 A 9/1999 Gray
5,970,986 A 10/1999 Bolz et al.
5,987,352 A 11/1999 Klein et al.
6,044,300 A 3/2000 Gray
6,051,017 A 4/2000 Loeb et al.
6,141,588 A 10/2000 Cox et al.
6,144,879 A 11/2000 Gray et al.
6,175,764 B1 1/2001 Loeb et al.
6,181,965 B1 1/2001 Loeb et al.
6,185,452 B1 2/2001 Schulman et al.
6,185,455 B1 2/2001 Loeb et al.
6,198,972 B1 3/2001 Hartlaub et al.
6,208,894 B1 3/2001 Schulman et al.
6,208,900 B1 3/2001 Ecker et al.
6,208,901 B1 * 3/2001 Hartung ..... A61N 1/368 607/18
6,214,032 B1 4/2001 Loeb et al.
6,240,316 B1 5/2001 Richmond et al.
6,315,721 B2 11/2001 Schulman et al.
6,348,070 B1 2/2002 Teissl et al.
6,366,811 B1 4/2002 Carlson
6,415,184 B1 7/2002 Ishikawa et al.
6,445,953 B1 9/2002 Bulkes et al.
6,580,947 B1 6/2003 Thompson
6,592,518 B2 7/2003 Denker et al.
6,628,989 B1 9/2003 Penner et al.
6,654,638 B1 11/2003 Sweeney
6,662,050 B2 12/2003 Olson
6,733,485 B1 5/2004 Whitehurst et al.
6,735,474 B1 5/2004 Loeb et al.
6,735,475 B1 5/2004 Whitehurst et al.
6,738,672 B2 5/2004 Schulman et al.
6,764,446 B2 7/2004 Wolinsky et al.
6,788,975 B1 9/2004 Whitehurst et al.
6,804,561 B2 10/2004 Stover
6,871,099 B1 3/2005 Whitehurst et al.
6,901,292 B2 5/2005 Hrdlicka et al.
6,907,285 B2 6/2005 Denker et al.
6,917,833 B2 7/2005 Denker et al.
6,925,328 B2 8/2005 Foster et al.
6,937,906 B2 8/2005 Terry et al.
6,941,171 B2 9/2005 Mann et al.
6,947,782 B2 9/2005 Schulman et al.
7,003,350 B2 2/2006 Denker et al.
7,006,864 B2 2/2006 Echt et al.
7,024,248 B2 4/2006 Penner et al.
7,047,074 B2 5/2006 Connelly et al.
7,050,849 B2 5/2006 Echt et al.
7,054,692 B1 5/2006 Whitehurst et al.
7,076,283 B2 7/2006 Cho et al.
7,082,328 B2 7/2006 Funke
7,082,336 B2 7/2006 Ransbury et al.
7,103,408 B2 9/2006 Haller et al.
7,114,502 B2 10/2006 Schulman et al.
7,120,992 B2 10/2006 He et al.
7,132,173 B2 11/2006 Daulton
7,167,751 B1 1/2007 Whitehurst et al.
7,177,698 B2 2/2007 Klosterman et al.
7,184,830 B2 2/2007 Echt et al.
7,198,603 B2 4/2007 Penner et al.
7,200,437 B1 4/2007 Nabutovsky et al.
7,203,548 B2 4/2007 Whitehurst et al.
7,212,863 B2 5/2007 Strandberg
7,214,189 B2 5/2007 Zdeblick
7,236,821 B2 6/2007 Cates et al.
7,236,829 B1 6/2007 Farazi et al.
7,242,981 B2 7/2007 Ginggen
7,260,436 B2 8/2007 Kilgore et al.
7,283,873 B1 10/2007 Park et al.
7,283,874 B2 10/2007 Penner
7,286,883 B2 10/2007 Schulman et al.
7,292,890 B2 11/2007 Whitehurst et al.
7,294,108 B1 11/2007 Bornzin et al.
7,295,879 B2 11/2007 Denker et al.
7,310,556 B2 12/2007 Bulkes
7,330,756 B2 2/2008 Marnfeldt
7,343,204 B2 3/2008 Schulman et al.
7,351,921 B1 4/2008 Haller et al.
7,363,082 B2 4/2008 Ransbury et al.
7,428,438 B2 9/2008 Parramon et al.
7,437,193 B2 10/2008 Parramon et al.
7,444,180 B2 10/2008 Kuzma et al.
7,450,996 B2 11/2008 MacDonald et al.
7,450,998 B2 11/2008 Zilberman et al.
7,493,172 B2 2/2009 Whitehurst et al.
7,513,257 B2 4/2009 Schulman et al.
7,519,421 B2 4/2009 Denker et al.
7,519,424 B2 4/2009 Dennis et al.
7,529,589 B2 5/2009 Williams et al.
7,532,932 B2 5/2009 Denker et al.
7,532,933 B2 5/2009 Hastings et al.
7,535,296 B2 5/2009 Bulkes et al.
7,555,345 B2 6/2009 Wahlstrand et al.
7,558,631 B2 7/2009 Cowan et al.
7,561,915 B1 7/2009 Cooke et al.
7,565,195 B1 7/2009 Kroll et al.
7,587,241 B2 9/2009 Parramon et al.
7,606,621 B2 10/2009 Brisken et al.
7,610,092 B2 10/2009 Cowan et al.
7,616,990 B2 11/2009 Chavan et al.
7,616,992 B2 11/2009 Dennis et al.
7,617,007 B2 11/2009 Williams et al.
7,627,371 B2 12/2009 Wang et al.
7,627,376 B2 12/2009 Dennis et al.
7,627,383 B2 12/2009 Haller et al.
7,630,767 B1 12/2009 Poore et al.
7,634,313 B1 12/2009 Kroll et al.
7,637,867 B2 12/2009 Zdeblick
7,640,060 B2 12/2009 Zdeblick
7,640,061 B2 12/2009 He et al.
7,647,109 B2 1/2010 Hastings et al.
7,650,186 B2 1/2010 Hastings et al.
7,706,892 B2 4/2010 Colvin et al.

(56) References Cited

U.S. PATENT DOCUMENTS 7,713,194 B2 5/2010 Zdeblick
7,734,343 B2 6/2010 Ransbury et al.
7,747,335 B2 6/2010 Williams
7,751,881 B2 7/2010 Cowan et al.
7,766,216 B2 8/2010 Daulton
7,771,838 B1 8/2010 He et al.
7,781,683 B2 8/2010 Haller et al.
7,809,438 B2 10/2010 Echt et al.
7,822,480 B2 10/2010 Park et al.
7,826,903 B2 11/2010 Denker et al.
7,840,282 B2 11/2010 Williams et al.
7,848,815 B2 12/2010 Brisken et al.
7,848,823 B2 12/2010 Drasler et al.
7,860,564 B2 12/2010 Root et al.
7,860,570 B2 12/2010 Whitehurst et al.
7,890,173 B2 2/2011 Brisken et al.
7,894,907 B2 2/2011 Cowan et al.
7,899,541 B2 3/2011 Cowan et al.
7,899,542 B2 3/2011 Cowan et al.
7,899,554 B2 3/2011 Williams et al.
7,904,167 B2 3/2011 Klosterman et al.
7,930,031 B2 4/2011 Penner
7,937,148 B2 5/2011 Jacobson
7,945,333 B2 5/2011 Jacobson
7,957,805 B2 6/2011 He
7,979,126 B2 7/2011 Payne et al.
7,991,467 B2 8/2011 Markowitz et al.
7,996,097 B2 8/2011 DiBernardo et al.
8,010,209 B2 8/2011 Jacobson
8,019,419 B1 9/2011 Panescu et al.
8,032,219 B2 10/2011 Neumann et al.
8,032,227 B2 10/2011 Parramon et al.
8,078,279 B2 12/2011 Dennis et al.
8,078,283 B2 12/2011 Cowan et al.
8,103,344 B2 1/2012 Bjorling
8,116,883 B2 2/2012 Williams et al.
8,126,561 B2 2/2012 Chavan et al.
8,127,424 B2 3/2012 Haller et al.
8,165,696 B2 4/2012 McClure et al.
8,185,212 B2 5/2012 Carbunaru et al.
8,204,595 B2 6/2012 Pianca et al.
8,224,449 B2 7/2012 Carbunaru et al.
8,239,045 B2 8/2012 Ransbury et al.
8,240,780 B1 8/2012 Klimes
8,295,939 B2 10/2012 Jacobson
8,301,242 B2 10/2012 Root et al.
8,301,262 B2 10/2012 Mi et al.
8,311,627 B2 11/2012 Root et al.
8,315,701 B2 11/2012 Cowan et al.
8,321,036 B2 11/2012 Brockway et al.
8,332,036 B2 12/2012 Hastings et al.
8,340,780 B2 12/2012 Hastings et al.
8,352,025 B2 1/2013 Jacobson
8,352,028 B2 1/2013 Wenger
8,359,098 B2 1/2013 Lund et al.
8,364,267 B2 1/2013 Schleicher et al.
8,364,276 B2 1/2013 Willis
8,364,278 B2 1/2013 Pianca et al.
8,364,280 B2 1/2013 Marnfeldt et al.
8,368,051 B2 2/2013 Ting et al.
8,374,696 B2 2/2013 Sanchez et al.
8,386,051 B2 2/2013 Rys
8,457,742 B2 6/2013 Jacobson
8,478,408 B2 7/2013 Hastings et al.
8,478,431 B2 7/2013 Griswold et al.
8,489,205 B2 7/2013 Stotts et al.
8,494,637 B2 7/2013 Cowan et al.
8,494,642 B2 7/2013 Cowan et al.
8,494,644 B2 7/2013 Cowan et al.
8,504,156 B2 8/2013 Bonner et al.
8,527,068 B2 9/2013 Ostroff
8,532,790 B2 9/2013 Griswold
8,541,131 B2 9/2013 Lund et al.
8,543,190 B2 9/2013 Wasson et al.
8,543,204 B2 9/2013 Demmer et al.
8,543,205 B2 9/2013 Ostroff
8,543,216 B2 9/2013 Carbunaru et al.
8,548,605 B2 10/2013 Ollivier
8,560,892 B2 10/2013 Nicholes
8,565,897 B2 10/2013 Regnier et al.
8,588,926 B2 11/2013 Moore et al.
8,626,294 B2 1/2014 Sheldon et al.
8,634,912 B2 1/2014 Bornzin et al.
8,634,919 B1 1/2014 Hou et al.
8,639,335 B2 1/2014 Peichel et al.
8,644,922 B2 2/2014 Root et al.
8,660,660 B2 2/2014 Dai et al.
8,670,842 B1 3/2014 Bornzin et al.
9,399,140 B2 7/2016 Cho et al.
2003/0114905 A1 6/2003 Kuzma
2003/0144704 A1 7/2003 Terry et al.
2003/0204212 A1 10/2003 Burnes et al.
2004/0015204 A1 1/2004 Whitehurst et al.
2004/0073267 A1 4/2004 Holzer
2004/0088012 A1 5/2004 Kroll et al.
2004/0093039 A1 5/2004 Schumert
2004/0122477 A1 6/2004 Whitehurst et al.
2004/0133242 A1 7/2004 Chapman et al.
2004/0147973 A1 7/2004 Hauser
2004/0162590 A1 8/2004 Whitehurst et al.
2004/0172089 A1 9/2004 Whitehurst et al.
2004/0215264 A1 10/2004 van Bentem
2004/0225332 A1 11/2004 Gebhardt et al.
2005/0038482 A1 2/2005 Yonce et al.
2005/0055061 A1 3/2005 Holzer
2005/0070962 A1 3/2005 Echt et al.
2005/0256549 A1 11/2005 Holzer
2005/0288717 A1 12/2005 Sunagawa
2006/0074449 A1 4/2006 Denker et al.
2006/0135999 A1 6/2006 Bodner et al.
2006/0136005 A1 6/2006 Brisken et al.
2006/0167496 A1 7/2006 Nelson et al.
2006/0173295 A1 8/2006 Zeijlemaker
2006/0173497 A1 8/2006 Mech et al.
2006/0241705 A1 10/2006 Neumann et al.
2006/0241732 A1 10/2006 Denker et al.
2006/0293591 A1 12/2006 Wahlstrand et al.
2006/0293714 A1 12/2006 Salo et al.
2007/0027508 A1 2/2007 Cowan et al.
2007/0060961 A1 3/2007 Echt et al.
2007/0073353 A1 3/2007 Rooney et al.
2007/0075905 A1 4/2007 Denker et al.
2007/0078490 A1 4/2007 Cowan et al.
2007/0088396 A1 4/2007 Jacobson
2007/0088397 A1 4/2007 Jacobson
2007/0106332 A1 5/2007 Denker et al.
2007/0106357 A1 5/2007 Denker et al.
2007/0118187 A1 5/2007 Denker et al.
2007/0129773 A1 6/2007 Bulkes
2007/0135883 A1 6/2007 Drasler et al.
2007/0150037 A1 6/2007 Hastings et al.
2007/0156204 A1 7/2007 Denker et al.
2007/0173890 A1 7/2007 Armstrong
2007/0185538 A1 8/2007 Denker et al.
2007/0210862 A1 9/2007 Denker et al.
2007/0219590 A1 9/2007 Hastings et al.
2007/0238975 A1 10/2007 Zeijlemaker
2007/0255327 A1 11/2007 Cho et al.
2007/0276444 A1 11/2007 Gelbart et al.
2007/0288076 A1 12/2007 Bulkes et al.
2007/0288077 A1 12/2007 Bulkes et al.
2007/0293904 A1 12/2007 Gelbart et al.
2007/0293908 A1 12/2007 Cowan et al.
2007/0293912 A1 12/2007 Cowan et al.
2007/0293913 A1 12/2007 Cowan et al.
2008/0009910 A1* 1/2008 Kraetschmer ..... A61N 1/368
607/9
2008/0033497 A1 2/2008 Bulkes et al.
2008/0039904 A1 2/2008 Bulkes et al.
2008/0051854 A1 2/2008 Bulkes et al.
2008/0058886 A1 3/2008 Williams
2008/0077184 A1 3/2008 Denker et al.
2008/0077188 A1 3/2008 Denker et al.
2008/0097529 A1 4/2008 Parramon et al.

(56) References Cited

U.S. PATENT DOCUMENTS

2008/0109054 A1 5/2008 Hastings et al.
2008/0119911 A1 5/2008 Rosero
2008/0132961 A1 6/2008 Jaax et al.
2008/0140154 A1 6/2008 Loeb et al.
2008/0154342 A1 6/2008 Digby et al.
2008/0234771 A1 9/2008 Chinchoy et al.
2008/0269816 A1 10/2008 Prakash et al.
2008/0269825 A1 10/2008 Chinchoy et al.
2008/0288039 A1 11/2008 Reddy
2008/0294208 A1 11/2008 Willis et al.
2008/0294210 A1 11/2008 Rosero
2008/0319502 A1 12/2008 Sunagawa et al.
2009/0024180 A1 1/2009 Kisker et al.
2009/0048583 A1 2/2009 Williams et al.
2009/0082827 A1 3/2009 Kveen et al.
2009/0082828 A1 3/2009 Ostroff
2009/0105779 A1 4/2009 Moore et al.
2009/0157146 A1 6/2009 Linder et al.
2009/0171408 A1 7/2009 Solem
2009/0192570 A1 7/2009 Jaax et al.
2009/0198293 A1 8/2009 Cauller et al.
2009/0198295 A1 8/2009 Dennis et al.
2009/0198308 A1 8/2009 Gross et al.
2009/0326601 A1 12/2009 Brisken et al.
2010/0049270 A1 2/2010 Pastore et al.
2010/0094367 A1 4/2010 Sen
2010/0161002 A1 6/2010 Aghassian et al.
2010/0179628 A1 7/2010 Towe et al.
2010/0198294 A1 8/2010 Kaiser
2010/0249883 A1 9/2010 Zdeblick
2010/0249885 A1 9/2010 Colvin et al.
2010/0286744 A1 11/2010 Echt et al.
2010/0304209 A1 12/2010 Lund et al.
2010/0305627 A1 12/2010 Anderson
2010/0305628 A1 12/2010 Lund et al.
2010/0305629 A1 12/2010 Lund et al.
2010/0312320 A1 12/2010 Faltys et al.
2011/0054555 A1 3/2011 Williams et al.
2011/0060392 A1 3/2011 Zdeblick et al.
2011/0071585 A1 3/2011 Ransbury et al.
2011/0071586 A1 3/2011 Jacobson
2011/0077707 A1 3/2011 Maile et al.
2011/0077708 A1 3/2011 Ostroff
2011/0077721 A1 3/2011 Whitehurst et al.
2011/0137378 A1 6/2011 Klosterman et al.
2011/0160792 A1 6/2011 Fishel
2011/0160801 A1 6/2011 Markowitz et al.
2011/0208260 A1 8/2011 Jacobson
2011/0245782 A1 10/2011 Berthiaume et al.
2011/0270339 A1 11/2011 Murray, III et al.
2011/0270340 A1 11/2011 Pellegrini et al.
2011/0282423 A1 11/2011 Jacobson
2011/0313490 A1 12/2011 Parramon et al.
2012/0059431 A1 3/2012 Williams et al.
2012/0081201 A1 4/2012 Norgaard et al.
2012/0095521 A1 4/2012 Hintz
2012/0095539 A1 4/2012 Khairkhahan et al.
2012/0101392 A1 4/2012 Bhunia et al.
2012/0109149 A1 5/2012 Bonner et al.
2012/0109236 A1 5/2012 Jacobson et al.
2012/0116489 A1 5/2012 Khairkhahan et al.
2012/0143271 A1 6/2012 Root et al.
2012/0158090 A1 6/2012 Chavan et al.
2012/0158111 A1 6/2012 Khairkhahan et al.
2012/0165827 A1 6/2012 Khairkhahan et al.
2012/0172690 A1 7/2012 Anderson et al.
2012/0172891 A1 7/2012 Lee
2012/0172892 A1 7/2012 Grubac et al.
2012/0172943 A1* 7/2012 Limousin ..... A61N 1/3627 607/5
2012/0179219 A1 7/2012 Kisker et al.
2012/0197352 A1 8/2012 Carbunaru et al.
2012/0197373 A1 8/2012 Khairkhahan et al.
2012/0215274 A1 8/2012 Koh et al.
2012/0232371 A1 9/2012 Mech et al.
2012/0271186 A1 10/2012 Siejko et al.
2012/0290021 A1 11/2012 Saurkar et al.
2012/0290025 A1 11/2012 Keimel
2012/0316622 A1 12/2012 Whitehurst et al.
2012/0323099 A1 12/2012 Mothilal et al.
2012/0330174 A1 12/2012 Carlson et al.
2013/0023975 A1 1/2013 Locsin
2013/0030483 A1 1/2013 Demmer et al.
2013/0035748 A1 2/2013 Bonner et al.
2013/0053907 A1 2/2013 Kirchner et al.
2013/0053913 A1 2/2013 Koh et al.
2013/0066169 A1 3/2013 Rys et al.
2013/0073004 A1 3/2013 Root et al.
2013/0079798 A1 3/2013 Tran et al.
2013/0079861 A1 3/2013 Reinert et al.
2013/0085407 A1 4/2013 Siejko et al.
2013/0103047 A1 4/2013 Steingisser et al.
2013/0103109 A1 4/2013 Jacobson
2013/0110127 A1 5/2013 Bornzin et al.
2013/0110219 A1 5/2013 Bornzin et al.
2013/0116529 A1 5/2013 Min et al.
2013/0116738 A1 5/2013 Samade et al.
2013/0116740 A1 5/2013 Bornzin et al.
2013/0123872 A1 5/2013 Bornzin et al.
2013/0123875 A1 5/2013 Varady et al.
2013/0131159 A1 5/2013 Ko et al.
2013/0131693 A1 5/2013 Berthiaume et al.
2013/0138006 A1 5/2013 Bornzin et al.
2013/0150695 A1 6/2013 Biela et al.
2013/0184790 A1 7/2013 Schleicher et al.
2013/0226259 A1 8/2013 Penner et al.
2013/0231710 A1 9/2013 Jacobson
2013/0234692 A1 9/2013 Liang et al.
2013/0235663 A1 9/2013 Walsh et al.
2013/0235672 A1 9/2013 Walsh et al.
2013/0238044 A1 9/2013 Penner
2013/0238056 A1 9/2013 Poore et al.
2013/0238072 A1 9/2013 Deterre et al.
2013/0238073 A1 9/2013 Makdissi et al.
2013/0238840 A1 9/2013 Walsh et al.
2013/0253309 A1 9/2013 Allan et al.
2013/0253344 A1 9/2013 Griswold et al.
2013/0253345 A1 9/2013 Griswold et al.
2013/0253346 A1 9/2013 Griswold et al.
2013/0253347 A1 9/2013 Griswold et al.
2013/0261497 A1 10/2013 Pertijs et al.
2013/0268042 A1 10/2013 Hastings et al.
2013/0274828 A1 10/2013 Willis
2013/0274847 A1 10/2013 Ostroff
2013/0282070 A1 10/2013 Cowan et al.
2013/0282073 A1* 10/2013 Cowan ..... A61N 1/37205 607/14
2013/0302665 A1 11/2013 Zhao et al.
2013/0303872 A1 11/2013 Taff et al.
2013/0324825 A1 12/2013 Ostroff et al.
2013/0325081 A1 12/2013 Karst et al.
2013/0331903 A1 12/2013 Lovett et al.
2013/0345770 A1 12/2013 Dianaty et al.
2014/0012342 A1 1/2014 Penner et al.
2014/0012344 A1 1/2014 Hastings et al.
2014/0018688 A1 1/2014 Song et al.
2014/0018876 A1 1/2014 Ostroff
2014/0018877 A1 1/2014 Demmer et al.
2014/0026016 A1 1/2014 Nicholes
2014/0031836 A1 1/2014 Ollivier
2014/0031837 A1 1/2014 Perryman et al.
2014/0039570 A1 2/2014 Carroll et al.
2014/0039578 A1 2/2014 Whithurst et al.
2014/0039588 A1 2/2014 Ok et al.
2014/0039591 A1 2/2014 Drasler et al.
2014/0046200 A1 2/2014 Patangay et al.
2014/0046395 A1 2/2014 Regnier et al.
2014/0058240 A1 2/2014 Mothilal et al.
2014/0072872 A1 3/2014 Hodgkinson et al.

(56) References Cited

U.S. PATENT DOCUMENTS

| | | | |
|---|---|---|---|
| 2014/0100627 | A1 | 4/2014 | Min |
| 2014/0121720 | A1 | 5/2014 | Bonner et al. |

FOREIGN PATENT DOCUMENTS

| | | | |
|---|---|---|---|
| EP | 1493460 | | 1/2005 |
| EP | 1493460 | B1 | 1/2005 |
| EP | 1541191 | A1 | 6/2005 |
| EP | 2526999 | A1 | 11/2012 |
| TW | 1251986 | B | 3/2006 |
| TW | 1252007 | B | 3/2006 |
| WO | 2005035048 | | 4/2005 |
| WO | 2006081434 | | 8/2006 |
| WO | 2006099425 | A1 | 9/2006 |
| WO | 2007117835 | | 10/2007 |
| WO | 2009006531 | A1 | 1/2009 |
| WO | 2009052480 | A2 | 4/2009 |
| WO | 2012057662 | A1 | 5/2012 |
| WO | 2012154599 | A2 | 11/2012 |
| WO | 2013080038 | A2 | 6/2013 |
| WO | 2013121431 | A1 | 8/2013 |
| WO | 2012150000 | | 11/2013 |
| WO | 2014046662 | | 3/2014 |

OTHER PUBLICATIONS

International Search Report and the Written Opinion from International Application No. PCT/US2015/040863, dated Oct. 9, 2015, 10 pages.

International Preliminary Report on Patentability from International Application No. PCT/US2015/040863, dated Feb. 9, 2017, 8 pp.

First Office Action, and translation thereof, from counterpart Chinese Patent Application No. 201580041159.0, dated Jul. 4, 2018, 20 pp.

Prosecution History from U.S. Appl. No. 14/579,105, dated from Nov. 27, 2015 through Apr. 5, 2016, 35 pp.

U.S. Pat. No. 8,116,861, Feb. 2011, Root et al (withdrawn).

(PCT/US2015/040863) PCT Notification of Transmittal of the International Search Report and the Written Opinion of the International Searching Authority, Mailed Oct. 9, 2015, 11 pages.

* cited by examiner

ATRIAL CONTRACTION DETECTION BY A VENTRICULAR LEADLESS PACING DEVICE FOR ATRIO-SYNCHRONOUS VENTRICULAR PACING

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application claims the benefit of U.S. Provisional Application No. 62/028,957, filed Jul. 25, 2014, the entire contents of which are incorporated herein by reference.

TECHNICAL FIELD

The disclosure relates to cardiac pacing, and more particularly, to cardiac pacing using a leadless pacing device.

BACKGROUND

An implantable pacemaker may deliver pacing pulses to a patient's heart and monitor conditions of the patient's heart. In some examples, the implantable pacemaker comprises a pulse generator and one or more electrical leads. The pulse generator may, for example, be implanted in a small pocket in the patient's chest. The electrical leads may be coupled to the pulse generator, which may contain circuitry that generates pacing pulses and/or senses cardiac electrical activity. The electrical leads may extend from the pulse generator to a target site (e.g., an atrium and/or a ventricle) such that electrodes at the distal ends of the electrical leads are positioned at a target site. The pulse generator may provide electrical stimulation to the target site and/or monitor cardiac electrical activity at the target site via the electrodes.

A leadless pacing device has also been proposed for sensing electrical activity and/or delivering therapeutic electrical signals to the heart. The leadless pacing device may include one or more electrodes on its outer housing to deliver therapeutic electrical signals and/or sense intrinsic depolarizations of the heart. The leadless pacing device may be positioned within or outside of the heart and, in some examples, may be anchored to a wall of the heart via a fixation mechanism.

SUMMARY

The disclosure describes a leadless pacing device (hereinafter, "LPD") that is configured for implantation in a ventricle of a heart of a patient, and is configured to deliver atrio-synchronous ventricular pacing based on detection of atrial contraction. More particularly, the LPD includes a motion sensor configured to generate a motion signal as a function of heart movement. The motion sensor may include one or more accelerometers, which may have a single axis, or multiple axes. The LPD is configured to analyze the motion signal within an atrial contraction detection window. The atrial contraction detection window begins upon completion of an atrial contraction detection delay period, which begins upon detection of activation of the ventricle. The LPD is configured to detect a contraction of an atrium of the heart based on the analysis of the motion signal within the atrial contraction detection window. If the LPD does not detect a ventricular depolarization subsequent to the atrial contraction, e.g., within an atrioventricular (AV) interval beginning when the atrial contraction was detected, the LPD delivers a ventricular pacing pulse. In some examples, the LPD is configured to deliver atrio-synchronous ventricular pacing using an electrical AV interval based on detection of atrial depolarizations via a plurality of electrodes of the LPD and, if the LPD is unable to detect atrial depolarizations, switch to delivering atrio-synchronous ventricular pacing using a mechanical AV interval, which may be shorter than the electrical AV interval, based on detection of atrial contractions.

In one example, a leadless pacing device is configured to provide atrio-synchronous ventricular pacing. The leadless pacing device comprises a plurality of electrodes, a motion sensor configured to generate a motion signal as a function of movement of a heart of a patient, a stimulation module coupled to the plurality of electrodes, wherein the stimulation module is configured to generate pacing pulses and deliver the pacing pulses to a ventricle of the heart via the plurality of electrodes, and an electrical sensing module coupled to the plurality of electrodes, wherein the electrical sensing module is configured to detect depolarizations of the ventricle within a cardiac electrogram sensed via the plurality of electrodes. The leadless pacing device further comprises a mechanical sensing module coupled to the motion sensor. The mechanical sensing module is configured to receive the motion signal from the motion sensor, identify an activation of the ventricle and, upon identification of the activation of the ventricle, initiate an atrial contraction detection delay period. The mechanical sensing module is further configured to analyze the motion signal within an atrial contraction detection window that begins upon completion of the atrial contraction detection delay period, and detect a contraction of an atrium of the heart based on the analysis of the motion signal within the atrial contraction detection window. The leadless pacing device further comprises a processing module configured to control the stimulation module to generate a pacing pulse and deliver the pacing pulse to the ventricle via the plurality of electrodes in response to the detection of the contraction of the atrium by the mechanical sensing module. The leadless pacing device further comprises a housing configured to be implanted within the ventricle, wherein the housing encloses the motion sensor, the stimulation module, the electrical sensing module, the mechanical sensing module, and the processing module.

In another example, a method for providing atrio-synchronous ventricular pacing by a leadless pacing device implanted within a ventricle of a heart of a patient comprises identifying an activation of the ventricle, upon identification of the activation of the ventricle, initiating an atrial contraction detection delay period, and analyzing a motion signal within an atrial contraction detection window that begins upon completion of the atrial contraction detection delay period. The motion signal is generated by a motion sensor of the leadless pacing device as a function of movement of the heart. The method further comprises detecting a contraction of an atrium of the heart based on the analysis of the motion signal within the atrial contraction detection window, and delivering a pacing pulse to the ventricle in response to the detection of the contraction of the atrium.

In another example, a leadless pacing device is configured to provide atrio-synchronous ventricular pacing. The leadless pacing device comprises means for generating a motion signal as a function of movement of a heart of a patient, means for identifying an activation of a ventricle of the heart, means for initiating an atrial contraction detection delay period upon identification of the activation of the ventricle, and means for analyzing the motion signal within an atrial contraction detection window that begins upon completion of the atrial contraction detection delay period. The leadless pacing device further comprises means for detecting a contraction of an atrium of the heart based on the analysis of the motion signal within the atrial contraction detection window, and means for delivering a pacing pulse to the ventricle in response to the detection of the contraction of the atrium.

In another example, a computer-readable storage medium comprises instructions stored thereon that, when executed by one or more programmable processors of a leadless pacing device configured to provide atrio-synchronous ventricular pacing, cause the one or more processors to identify an activation of the ventricle, upon identification of the activation of the ventricle, initiate an atrial contraction detection delay period, and analyze a motion signal within an atrial contraction detection window that begins upon completion of the atrial contraction detection delay period. The motion signal is generated by a motion sensor of the leadless pacing device as a function of movement of the heart. The instructions further cause the one or more processors to detect a contraction of an atrium of the heart based on the analysis of the motion signal within the atrial contraction detection window, and control delivery of a pacing pulse to the ventricle in response to the detection of the contraction of the atrium.

The details of one or more examples are set forth in the accompanying drawings and the description below. Other features, objects, and advantages will be apparent from the description and drawings, and from the claims.

DETAILED DESCRIPTION

Figure 1:
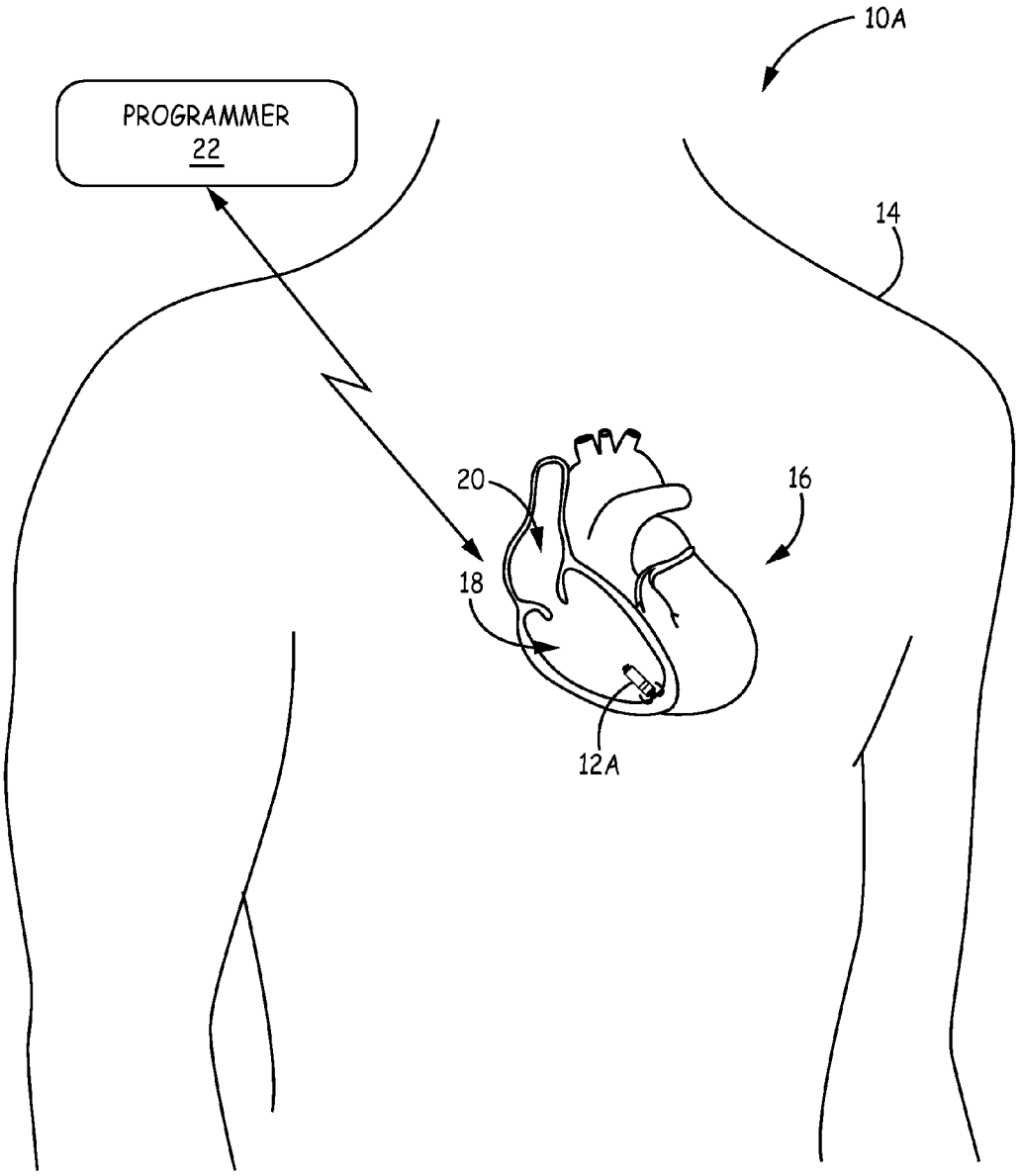
FIG. 1 is a conceptual diagram illustrating an example leadless pacing system that comprises an example leadless pacing device configured to deliver atrio-synchronous ventricular pacing based on atrial contraction detection implanted within a patient.

Typically, dual-chamber implantable pacemakers are implanted within a pocket within the patient's chest, and coupled to a right-atrial lead and a right-ventricular lead. The right-atrial lead extends from the implantable pacemaker in the pocket to the right atrium of the patient's heart, and positions one or more electrodes within the right atrium. The right-ventricular lead extends from the implantable pacemaker in the pocket to the right ventricle of the patient's heart, and positions one or more electrodes within the right ventricle.

Such dual-chamber implantable pacemakers sense respective cardiac electrical activity, e.g., respective cardiac electrograms, via the one or more electrodes implanted within the right atrium and the one or more electrodes implanted within the right ventricle. In particular, such dual-chamber implantable pacemakers detect intrinsic atrial depolarizations via the one or more electrodes implanted within the right atrium, and intrinsic ventricular depolarizations via the one or more electrodes implanted within the right ventricle. The implantable pacemakers may also deliver pacing pulses to the right atrium and the right ventricle via the one or more electrodes in the right atrium and the right ventricle, respectively. Due to the ability to sense both atrial and ventricular electrical activity, such dual-chamber implantable pacemakers may be able to provide atrio-synchronous ventricular pacing. For patients with intermittent AV node conduction, it may be preferable to inhibit ventricular pacing and allow an intrinsic ventricular depolarization to occur for a time, referred to as the AV interval, after an intrinsic atrial depolarization or atrial pace. Such atrio-synchronous pacing in dual-chamber implantable pacemakers may be according to the VDD or DDD programming modes, which have been used to treat patients with various degrees of AV block.

Implantable cardiac leads and the pocket in which pacemakers are implanted may be associated with complications. To avoid such complications leadless pacing devices sized to be implanted entirely within one chamber, e.g., the right ventricle, of the heart have been proposed. Some proposed leadless pacemakers include a plurality of electrodes that are affixed to, or are a portion of, the housing of the leadless pacing device.

Some proposed leadless pacing devices are capable of sensing intrinsic depolarizations of, and delivering pacing pulses to, the chamber of the heart in which they are implanted via the plurality of electrodes. However, because they are not coupled to electrodes in any other chamber, some proposed leadless pacing devices are incapable of sensing intrinsic depolarizations of, and delivering pacing pulses to, another chamber of the heart. Consequently, when implanted in the right ventricle, for example, such proposed leadless pacing devices may be unable to sense intrinsic atrial depolarizations of the atria, and may be limited to delivery of ventricular pacing according to an asynchronous ventricular pacing, e.g., according to a VVI or VVIR mode.

FIG. 1 is a conceptual diagram illustrating an example leadless pacing system 10A that comprises an example leadless pacing device (LPD) 12A that is configured to deliver atrio-synchronous ventricular pacing based on atrial contraction detection. In the example of FIG. 1, LPD 12A is implanted within right ventricle 18 of heart 16 of patient 14. More particularly, LPD 12A is fixed or attached to the inner wall of the right ventricle 18 proximate to the apex of the right ventricle in the example of FIG. 1. In other examples, LPD 12A may be fixed to the inner wall of right ventricle 18 at another location, e.g., on the intraventricular septum or free-wall of the right ventricle, or may be fixed to the outside of heart 16, i.e., epicardially, proximate to right ventricle 18. In other examples, LPD may be fixed within, on, or near the left-ventricle of heart 16.

LPD 12A includes a plurality of electrodes that are affixed to, or are a portion of, the housing of LPD 12A. LPD 12A senses electrical signals associated with depolarization and repolarization of heart 16, i.e., a cardiac electrogram signal, via the electrodes. LPD 12A also delivers cardiac pacing pulses to right ventricle 18 via the electrodes.

LPD 12A detects depolarizations of right ventricle 18 within the cardiac electrogram. In some examples, LPD 12A is not configured to detect intrinsic depolarizations of an atrium, e.g., right atrium 20, or the atria of heart 16 generally, within the cardiac electrogram signal. In other examples, LPD 12A is configured to detect atrial depolarizations within the cardiac electrogram signal. In some examples, LDP 12A is configured to detect atrial depolarizations with the cardiac electrogram signal, but may, at times, be unable to reliably detect atrial depolarizations, e.g., due to the quality of the cardiac electrogram signal, or the relatively small magnitude of the atrial depolarizations within a cardiac electrogram signal sensed via electrodes disposed within right ventricle 18. LPD 12A is configured to detect mechanical contractions of an atrium, e.g., right atrium 20, or the atria of heart 16 generally, e.g., as an alternative to sensing electrical depolarizations of right atrium 20. In this manner, LPD 12A may be configured to deliver atrio-synchronous ventricular pacing to right ventricle 18 even when not configured, or unable, to detect atrial depolarizations.

As described in greater detail below, LPD 12A includes a motion sensor configured to generate a motion signal as a function of movement of a heart of a patient. LPD 12A is configured to identify an activation event of right ventricle 18, and analyze the motion signal within an atrial contraction detection window that begins upon completion of an atrial contraction detection delay period that is initiated upon detection of the activation of the ventricle. The activation of the ventricle may be an intrinsic depolarization of the ventricle or delivery of a pacing pulse to the ventricle. In some examples, LPD 12A may be configured to detect contraction of right ventricle 18 based on the motion signal, and identify activation of the ventricle based on the detected ventricular contraction.

LPD 12A is configured to detect an atrial contraction based on the analysis of the motion signal within the atrial contraction detection window. If a subsequent intrinsic depolarization of right ventricle 18 is not detected, e.g., within an AV interval beginning when the atrial contraction was detected, LPD 12A is further configured to deliver the pacing pulse to right ventricle 18. In this manner, LPD 12A is configured to deliver atrio-synchronous pacing to right ventricle 18 based on detection of atrial contractions.

In some examples, LPD 12A is configured to assess the efficacy of the delivery of atrio-synchronous pacing to right ventricle 18. For example, LPD 12A may detect a resulting contraction of right ventricle 18 based on the motion signal after delivery of a pacing pulse to the right ventricle, and determine whether the delivery of the pacing pulse to the right ventricle was effective based on the detection of the contraction of the right ventricle. In some examples, LPD 12A may determine one or more metrics of the ventricular contraction, such as a timing or amplitude of the ventricular contraction, and adjust the delivery of the ventricular pacing based on the one or more metrics. LPD 12A may adjust the AV interval, which begins upon detection of atrial contraction, based on the one or more metrics, as one example.

In addition to the motion of the heart, a motion signal generated by the motion sensor of LPD 12A may include more general motion of patient 14 due to patient activity or experienced by patient, e.g., driving in a car. Such motion of patient 14 may interfere with the ability of LPD 12A to detect atrial contractions. In some examples, LPD 12A is configured to determine an amount of motion of patient 14 based on the motion signal, and change from delivery of ventricular pacing according to an atrio-synchronous pacing mode to delivery of ventricular pacing according to an asynchronous pacing mode in response to determining that the amount of patient motion exceeds a threshold. In some examples, LPD 12A is additionally or alternatively configured to change from delivery of ventricular pacing according to an atrio-synchronous pacing mode to delivery of ventricular pacing according to an asynchronous pacing mode in response to determining that the heart rate is relatively high and/or irregular, e.g., based on intervals between successive intrinsic ventricular depolarizations and a stored threshold value, such as approximately 100 beats-per-minute (bpm). In some examples, LPD 12A is additionally or alternatively configured to change from delivery of ventricular pacing according to an atrio-synchronous pacing mode to delivery of ventricular pacing according to an asynchronous pacing mode in response to determining that an atrial contraction was not detected during a predetermined number of cardiac cycles. According to an asynchronous ventricular pacing mode, e.g., VVI or VVIR, LPD 12A delivers a ventricular pacing pulse if an intrinsic ventricular depolarization is not detected within a VV interval that begins when a previous intrinsic ventricular depolarization was detected, or a previous ventricular pacing pulse was delivered.

As illustrated in FIG. 1, leadless pacing system 10A also includes a medical device programmer 22, which is configured to program LPD 12A and retrieve data from LPD 12A. Programmer 22 may be a handheld computing device, desktop computing device, a networked computing device, or any other type of computing device, as examples. Programmer 22 may include a computer-readable storage medium having instructions that cause a processor of programmer 22 to provide the functions attributed to programmer 22 in the present disclosure. LPD 12A may wirelessly communicate with programmer 22. For example, LPD 12A may transfer data to programmer 22 and may receive data from programmer 22. Programmer 22 may also wirelessly program and/or wirelessly charge LPD 12A.

Data retrieved from LPD 12A using programmer 22 may include cardiac electrograms and motion signals stored by LPD 12A that indicate the electrical and mechanical activity of heart 16, and marker channel data that indicates the occurrence and timing of sensing, diagnosis, and therapy events associated with LPD 12A, e.g., detection of atrial and ventricular depolarizations, atrial and ventricular contractions, and delivery of pacing pulses. Data transferred to LPD 12A using programmer 22 may include, for example, operational programs for LPD 12A that causes LPD 12A to operate as described herein. As examples, data transferred to LPD 12A using programmer 22 may include lengths of any AV intervals, atrial contraction detection delay periods, and atrial contraction detection windows described herein, any threshold values, such as for detecting atrial and/or ventricular contractions, or programming used by LPD 12A to determine such values based on determined parameters of heart 16, patient 14, or LPD 12A.

Figure 2:
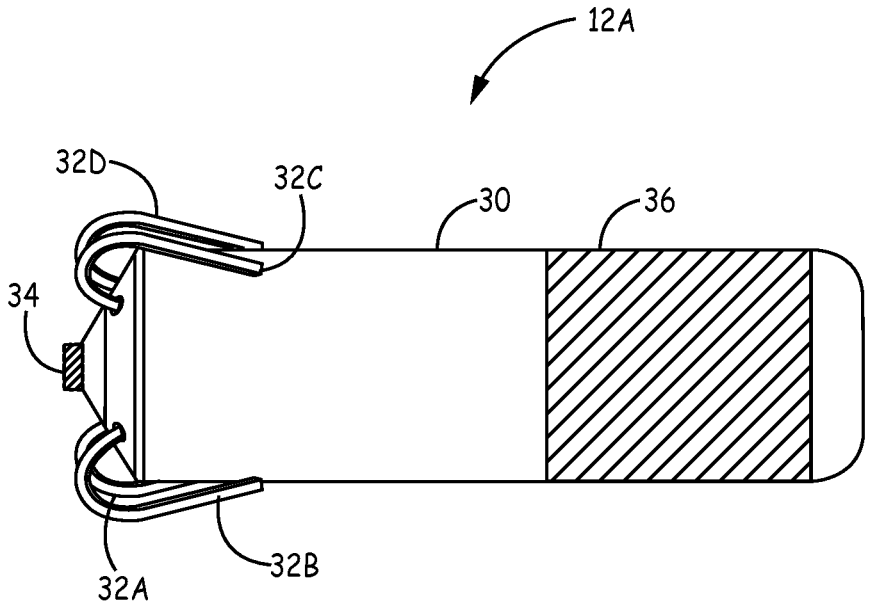
FIG. 2 is a conceptual diagram further illustrating the example leadless pacing device of FIG. 1.

FIG. 2 is a conceptual diagram further illustrating LPD 12A. As illustrated in FIG. 2, LPD 12A includes an outer housing 30, fixation times 32A-32D (collectively "fixation tines 32"), and electrodes 34 and 36. Outer housing 30 is configured to allow, e.g., has a size and form factor that allows, LPD 12A to be entirely implanted within a chamber of heart 16, such as right ventricle 18. As illustrated in FIG. 2, housing 30 may have a cylindrical (e.g., pill-shaped) form factor in some examples. Housing 30 may be hermetically sealed to prevent ingress of fluids into the interior of housing 30.

Fixation tines 32 extend from outer housing 30, and are configured to engage with cardiac tissue to substantially fix a position of housing 30 within a chamber of heart 16, e.g., at or near an apex of right ventricle 18. Fixation tines 32 are configured to anchor housing 30 to the cardiac tissue such that LPD 12A moves along with the cardiac tissue during cardiac contractions. Fixation tines 32 may be fabricated from any suitable material, such as a shape memory material (e.g., Nitinol). The number and configuration of fixation tines 32 illustrated in FIG. 2 is merely one example, and other numbers and configurations of fixation tines for anchoring an LPD housing to cardiac tissue are contemplated. Additionally, although LPD 12A includes a plurality of fixation tines 32 that are configured to anchor LPD 12A to cardiac tissue in a chamber of a heart, in other examples, LPD 12A may be fixed to cardiac tissue using other types of fixation mechanisms, such as, but not limited to, barbs, coils, and the like.

LPD 12A is configured to sense electrical activity of heart 16, i.e., a cardiac electrogram, and deliver pacing pulses to right ventricle 18, via electrodes 34 and 36. Electrodes 34 and 36 may be mechanically connected to housing 30, or may be defined by a portion of housing 30 that is electrically conductive. In either case, electrodes are electrically isolated from each other. Electrode 34 may be referred to as a tip electrode, and fixation tines 32 may be configured to anchor LPD 12A to cardiac tissue such that electrode 34 maintains contact with the cardiac tissue. Electrode 36 may be defined by a conductive portion of housing 30 and, in some examples, may define at least part of a power source case that houses a power source (e.g., a battery) of LPD 12A. In some examples, a portion of housing 30 may be covered by, or formed from, an insulative material to isolate electrodes 34 and 36 from each other and/or to provide a desired size and shape for one or both of electrodes 34 and 36.

Outer housing 30 houses electronic components of LPD 12A, e.g., an electrical sensing module for sensing cardiac electrical activity via electrodes 34 and 36, a motion sensor, a mechanical sensing module for detecting cardiac contractions, and an electrical stimulation module for delivering pacing pulses via electrodes 34 and 36. Electronic components may include any discrete and/or integrated electronic circuit components that implement analog and/or digital circuits capable of producing the functions attributed to an LPD described herein. Additionally, housing 30 may house a memory that includes instructions that, when executed by one or more processors housed within housing 30, cause LPD 12A to perform various functions attributed to LPD 12A herein. In some examples, housing 30 may house a communication module that enables LPD 12A to communicate with other electronic devices, such as medical device programmer 22. In some examples, housing 30 may house an antenna for wireless communication. Housing 30 may also house a power source, such as a battery.

Figure 3:
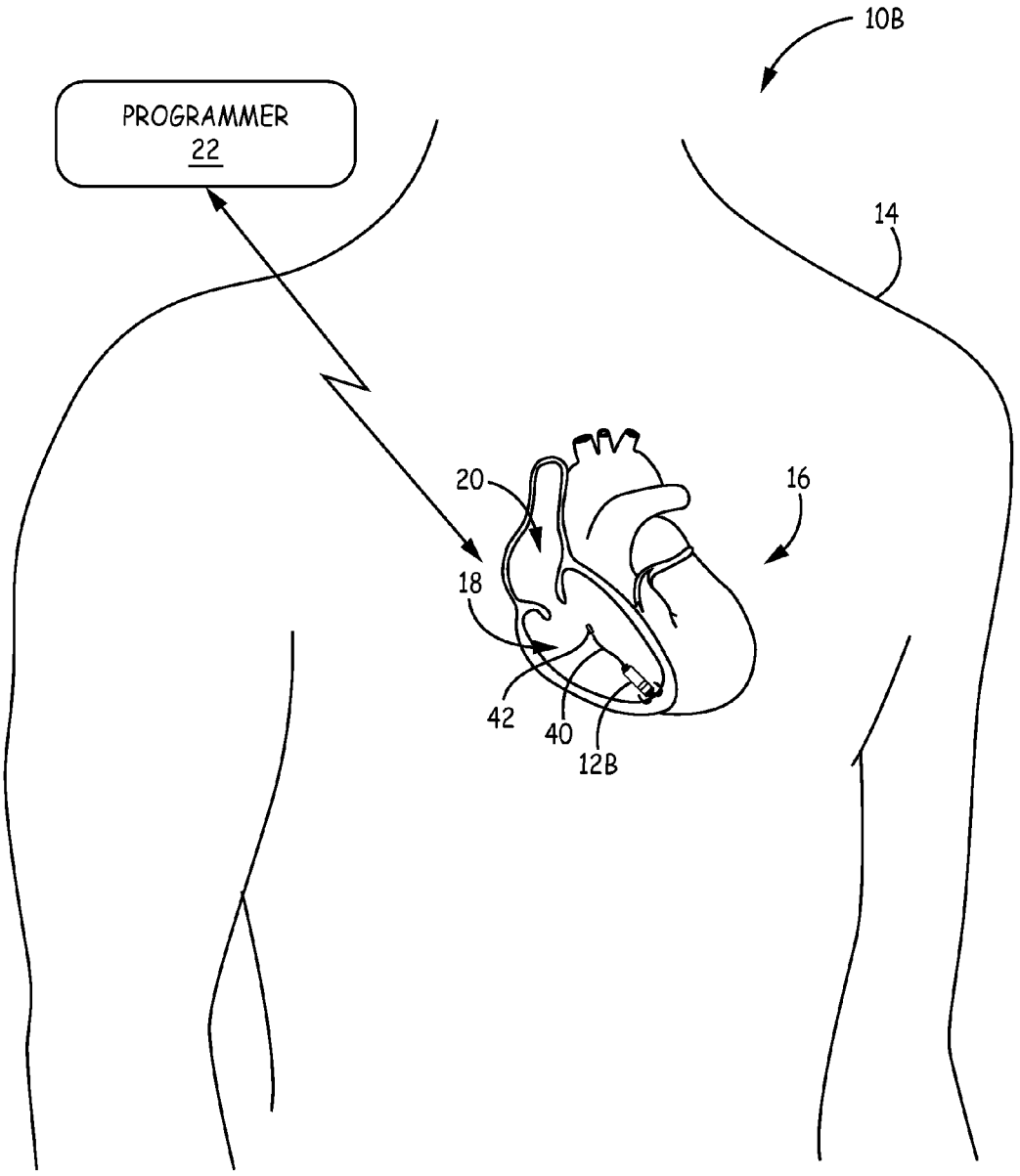
FIG. 3 is a conceptual diagram illustrating another example leadless pacing system that comprises another example leadless pacing device configured to deliver atrio-synchronous ventricular pacing based on atrial contraction detection implanted within a patient.

FIG. 3 is a conceptual diagram illustrating another example leadless pacing system 10B that comprises another example LPD 12B configured to deliver atrio-synchronous ventricular pacing based on atrial contraction detection. Leadless pacing system 10B and LPD 12B may be substantially the same as leadless pacing system 10A and LPD 12A described above with respect to FIGS. 1 and 2. Unlike LPD 12A, however, LPD 12B includes a sensing extension 40 that includes an electrode 42. In some examples, sensing extension 40 may include one or more additional electrodes having the same polarity as electrode 42. Although not illustrated in FIG. 3, LPD 12B may include an electrode 34, but may not include electrode 36, as described above with respect to LPD 12A and FIG. 2.

Electrode 42 is electrically connected to electronics within a housing of LPD 12B (e.g., an electrical sensing module and a stimulation module) via an electrical conductor of sensing extension 40. In some examples, the electrical conductor of sensing extension 40 is connected to the electronics via an electrically conductive portion of the housing of LPD 12B, which may correspond to electrode 36 of LPD 12A (FIG. 2), but may be substantially completely insulated (e.g., completely electrically insulated or nearly completely electrically insulated). Substantially completely electrically insulating the conductive portion of the housing may allow an electrical sensing module of LPD 12B to sense electrical cardiac activity with electrode 42 of sensing extension 40, rather than the conductive portion of the housing.

Additionally, as shown in FIG. 3, sensing extension 40 extends away from LPD 12, which enables electrode 42 to be positioned relatively close to right atrium 20. As a result, a cardiac electrogram sensed by LPD 12B via electrodes 34 (FIGS. 2) and 42 may include a higher amplitude far-field atrial depolarization signal than a cardiac electrogram sensed by LPB 12A via electrodes 34 and 36 (FIG. 2). In this way, sensing extension 40 may facilitate detection of atrial depolarizations when LPD 12B is implanted in right ventricle 18. In some examples, sensing extension 40 is sized to be entirely implanted within right ventricle 18. In other examples, sensing extension 40 is sized to extend into right atrium 20.

LPD 12B is configured to detect atrial depolarizations within a cardiac electrogram signal. Accordingly, LPD 12B may be configured to deliver atrio-synchronous ventricular pacing based on detection of atrial depolarizations. For example, LPD 12B may be configured to deliver a pacing pulse to right ventricle 18 if an intrinsic depolarization of right ventricle 18 is not detected within an AV interval after detection of a depolarization of right atrium 20.

However, despite sensing extension 40, LPD 12B may, at times, be unable to detect depolarizations of right atrium 20, e.g., due to reduced cardiac electrogram signal quality. Reduced cardiac electrogram signal quality may include reduced amplitude of the atrial component of the cardiac electrogram signal and/or increased noise. Reduced cardiac electrogram signal quality may be caused by, for example, movement of sensing extension 40 relative to right atrium 20, which may be caused by posture or activity of patient 14, or other conditions of patient 14, heart 16, and/or LPD 12B. Consequently, LPD 12B is also configured to detect atrial contractions, and deliver atrio-synchronous ventricular pacing based on the atrial contractions, as described with respect to LPD 12A.

In some examples, LPD 12B is configured to determine that an atrial depolarization was not detected during a cardiac cycle. For example, LPD 12B may be configured to determine that an atrial depolarization was not detected between consecutive ventricular depolarizations. In some examples, in response to determining that a depolarization of the atrium was not detected during a predetermined number of cardiac cycles, LPD 12B is configured to switch from delivering atrio-synchronous ventricular pacing based on detection of atrial depolarization and using an electrical AV interval, to delivering atrio-synchronous ventricular pacing based on detection of atrial contractions and using a mechanical AV interval. Because mechanical contraction of the atrium occurs after electrical depolarization of the atrium, the mechanical AV interval may be shorter than the electrical AV interval.

Figure 4:
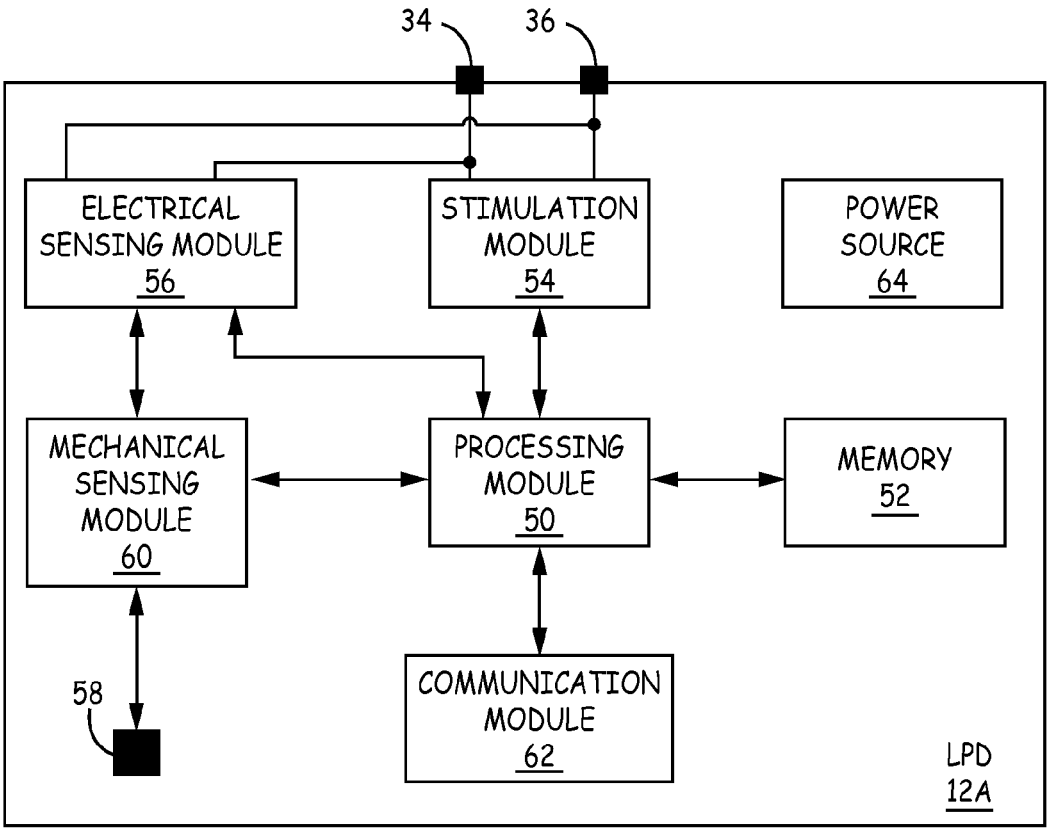
FIG. 4 is a functional block diagram illustrating an example configuration of a leadless pacing device configured to deliver atrio-synchronous ventricular pacing based on atrial contraction detection.

FIG. 4 is a functional block diagram illustrating an example configuration of an LPD 12A to deliver atrio-synchronous ventricular pacing based on atrial contraction detection. LPD 12B of FIG. 3 may have a similar configuration. However, electrode 36 of LPD 12A may be replaced by electrode 42 of LPD 12B, which may be positioned a greater distance away from electrode 34 and LPD 12B, as described above with respect to FIG. 3.

LPD 12A includes a processing module 50, memory 52, stimulation module 54, electrical sensing module 56, motion sensor 58, mechanical sensing module 60, communication module 62, and power source 64. Power source 64 may include a battery, e.g., a rechargeable or non-rechargeable battery.

Modules included in LPD 12A represent functionality that may be included in LPD 12A of the present disclosure. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, and the like. The functions attributed to the modules herein may be embodied as one or more processors, hardware, firmware, software, or any combination thereof. Depiction of different features as modules is intended to highlight different functional aspects, and does not necessarily imply that such modules must be realized by separate hardware or software components. Rather, functionality associated with one or more modules may be performed by separate hardware or software components, or integrated within common or separate hardware or software components.

Processing module 50 may include any one or more of a microprocessor, a controller, a digital signal processor (DSP), an application specific integrated circuit (ASIC), a field-programmable gate array (FPGA), or equivalent discrete or integrated logic circuitry. In some examples, processing module 50 includes multiple components, such as any combination of one or more microprocessors, one or more controllers, one or more DSPs, one or more ASICs, or one or more FPGAs, as well as other discrete or integrated logic circuitry. Additionally, although illustrated as separate functional components in FIG. 4, some or all of the functionality attributed to stimulation module 54, electrical sensing module 56, mechanical sensing module 60, and communication module 62 may implemented in the one or more combination of one or more microprocessors, one or more controllers, one or more DSPs, one or more ASICs, one or more FPGAs, and/or other discrete or integrated logic circuitry that implements processing module 50.

Processing module 50 may communicate with memory 52. Memory 52 may include computer-readable instructions that, when executed by processing module 50, cause processing module 50 and any other modules of LPD 12A to perform the various functions attributed to them herein. Memory 52 may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device.

Stimulation module 54 and electrical sensing module 56 are electrically coupled to electrodes 34, 36. Processing module 50 is configured to control stimulation module 54 to generate and deliver pacing pulses to heart 16 (e.g., right ventricle 18 in the example shown in FIG. 1) via electrodes 34, 36. In addition, processing module 50 is configured to control electrical sensing module 56 monitor a signal from electrodes 34, 36 in order to monitor electrical activity of heart 16. Electrical sensing module 56 may include circuits that acquire an electrical signal from electrodes 34, 36, as well as circuits to filter, amplify, and otherwise process the electrical signal. The electrical signal includes intrinsic cardiac electrical activity, such as depolarizations and repolarizations of the ventricles and, in some cases, depolarizations of the atria, and may be referred to as a cardiac electrogram signal. Electrical sensing module 56 detects ventricular depolarizations within the cardiac electrogram signal and, in some examples, detects atrial depolarizations within the cardiac electrogram signal.

LPD 12A also includes motion sensor 58. In some examples, motion sensor 58 comprises one or more accelerometers. In some examples, motion sensor 58 comprises a plurality of accelerometers, e.g., three accelerometers, each of which is oriented to detect motion in the direction of a respective axis or vector. The axes or vectors may be orthogonal. In other examples, motion sensor 58 may comprises one or more different sensors that generate a signal as a function of motion, instead of or in addition to the one or more accelerometers, such as gyros, mercury switches, or bonded piezoelectric crystals.

Mechanical sensing module 60 includes circuitry to receive the motion signal from motion sensor 58, as well as circuits to filter, amplify, and otherwise process the motion signal. Because LPD 12A is affixed to heart 16, motion sensor 60 generates a motion signal that varies as a function of motion of the heart, including motion associated with the contraction of the atria, and motion associated with the subsequent contraction of the ventricles. Because LPD 12A is implanted within patient 14, the motion signal generated by motion sensor 58 also varies as a function of any motion of (or experienced by) the patient, e.g., due to patient activity.

As described in greater detail below, mechanical sensing module 60 analyzes the motion signal generated by motion sensor 58 to detect contraction of an atrium. Mechanical sensing module 60 may also analyze the motion signal to detect ventricular contraction. To detect atrial or ventricular contractions, mechanical sensing module 60 may filter the motion signal to exclude components other than cardiac motion, e.g., components of the motion signal associated with motion engaged in or experienced by patient 14. For example, to detect contraction of an atrium, mechanical sensing module 60 may high-pass filter the motion signal, e.g., to exclude frequencies lower than about 40 Hz. As another example, to detect contraction of a ventricle, mechanical sensing module 60 may high-pass filter the motion signal, e.g., to exclude frequencies lower than about 60 Hz.

Mechanical sensing module 60 may also analyze the motion signal to detect other parameters of patient 14, such as patient activity level. To detect patient activity level, mechanical sensing module 60 may filter the motion signal to exclude components other than those resulting from patient activity, such as components associated with cardiac contraction. For example, mechanical sensing module 60 may low-pass filter the motion signal generated by motion sensor 58, e.g., to exclude frequencies above about 40 Hz. Processing module 50 may control stimulation module 54 to deliver rate responsive ventricular pacing based on the activity level determined by motion sensing module 60. For example, processing module 50 may adjust an AV interval based on the activity level.

In examples in which motion sensor 58 includes a plurality of accelerometers or other sensors, a motion signal generated by motion sensor 58 may include one or more of the signals generated by the sensors, respectively, or a combination of one or more of the respective signals, which may be referred to as component signals of the motion signal. Mechanical sensing module 60 may derive the motion signal based on one or more of the component signals according to a sensing vector, where different sensing vectors specify a different one or more of the component signals. In some examples, mechanical sensing module 60 is configured to derive the motion signal according to a variety of different sensing vectors. In some examples, mechanical sensing module 60 may be configured to sense different parameters or events, e.g., atrial contractions, ventricular contractions, and patient activity, using different sensing vectors. In some examples, mechanical sensing module 60 is configured to detect an event or parameter, e.g., atrial contraction, according to a plurality of sensing vectors, and identify one or more sensing vectors that provide adequate detection of the event.

Communication module 62 may include any suitable hardware (e.g., an antenna), firmware, software, or any combination thereof for communicating with another device, such as programmer 22 (FIGS. 1 and 3) or a patient monitor. Under the control of processing module 50, communication module 62 may receive downlink telemetry from and send uplink telemetry to other devices, such as programmer 22 or a patient monitor, with the aid of an antenna included in communication module 62.

Memory 52 may include data recorded by LPD 12A, e.g., cardiac electrograms, motion signals, heart rates, information regarding detection of atrial contractions, ventricular pacing efficacy, etc. Under the direction of processing module 50, communication module 62 may transfer data recorded by LDP 12A to another device, such as programmer 22. Memory 52 may also store programming data received by processing module 50 from another device, such as programmer 22, via communication module 62. The programming data stored in memory 52 may include, as examples, lengths of any AV intervals, atrial contraction detection delay periods, and atrial contraction detection windows described herein. The programming data stored in memory 52 may additionally or alternatively include any threshold values described herein, such as for detecting atrial and/or ventricular contractions, determining whether pacing is efficacious, or determining whether atrio-synchronous ventricular pacing should by suspended in favor of asynchronous pacing. The programming data stored in memory 52 may additionally or alternatively include data used by processing module 50 to determine any values described herein, e.g., based determined parameters of heart 16, patient 14, or LPD 12A.

Figure 5:
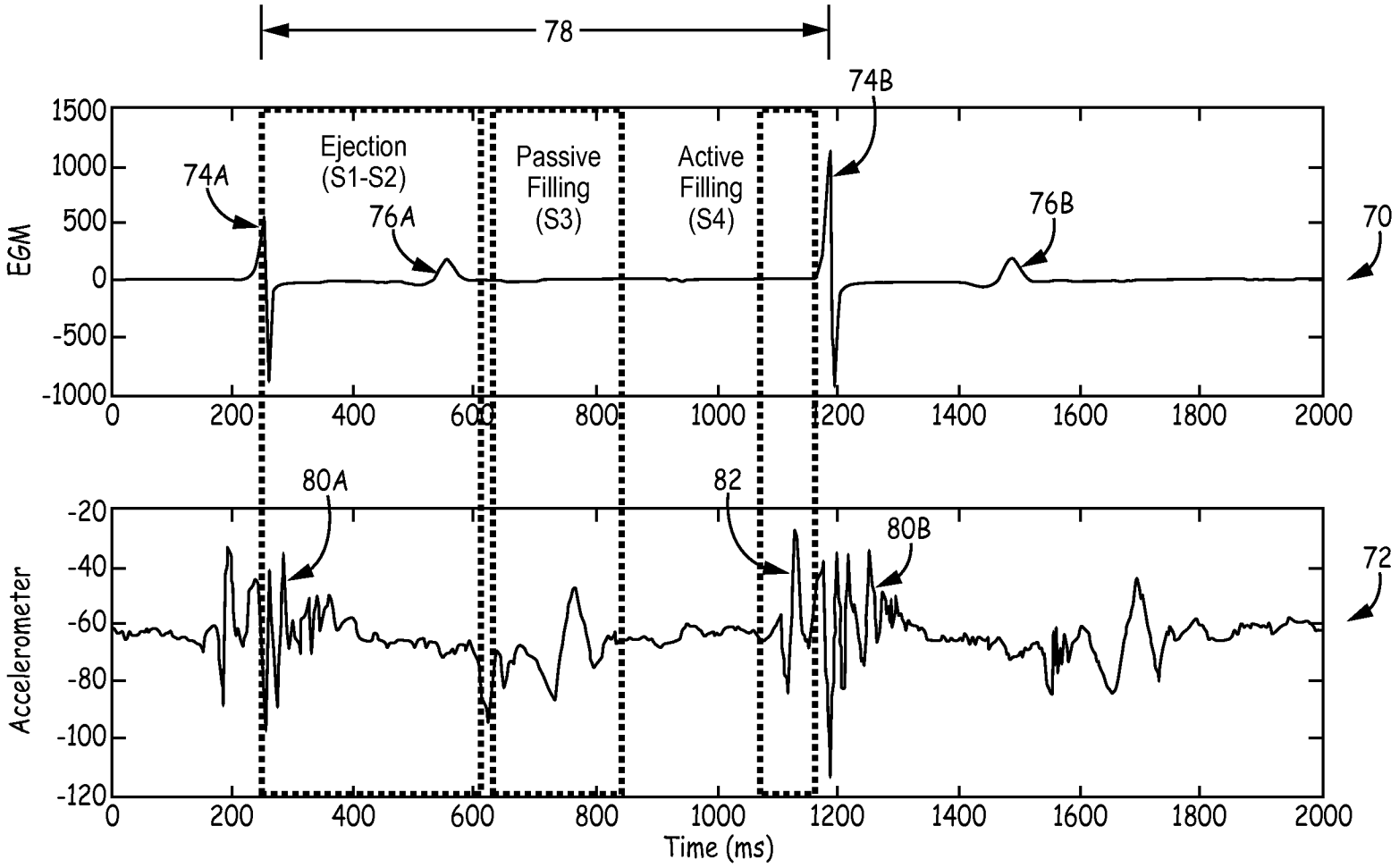
FIG. 5 is a graph illustrating a cardiac electrogram and a corresponding motion signal.

FIG. 5 is a graph illustrating a cardiac electrogram signal 70 and a corresponding motion signal 72 generated by one or more accelerometers. Cardiac electrogram signal 70 includes ventricular depolarizations (R-waves) 74A and 74B, and corresponding ventricular repolarizations (T-waves) 76A and 76B. A cardiac cycle 78 may be defined as the period from one ventricular depolarization 74A to the next ventricular depolarization 74B, or the period between any repeating fiducial features of cardiac electrogram signal 70 or motion signal 72.

As illustrated by FIG. 5, cardiac cycle 78 includes an ejection phase, which may also be referred to as systole. During the ejection phase a ventricular contraction 80A occurs as a result of ventricular depolarization 74A. The S1 and S2 heart sounds, which are associated with ventricular contraction, occur at the beginning and end, respectively, of the ejection phase. The S1 and S2 heart sounds are produced by closing of the atrioventricular values and semilunar valves of heart 16, respectively.

After the ejection phase, cardiac cycle 78 includes a passive filing stage during diastole, during which passive filling of the ventricles may produce the S3 heart sound. Additionally, near the end of diastole, an atrial contraction 82 occurs, actively filling of the ventricles. The active filing of the ventricles may produce the S4 heart sound. The atrial depolarization that resulted in atrial contraction 82 is not present in cardiac electrogram 70. Another cardiac cycle begins with ventricular depolarization 74B, and the resulting ventricular contraction 80B.

Mechanical sensing module 60 detects atrial contractions, and may also detect ventricular contractions, based on an analysis of a motion signal generated by motion sensor 58. The motion signal generated by motion sensor 58 may vary based on the movement of tissue of heart 16, as well as any associated mechanical perturbations or vibrations, during contraction of heart 16. Mechanical perturbations or vibrations may include those associated with the S1-S4 hearts sounds discussed above. For example, mechanical sensing module 60 may detect an atrial contraction based on features in motion signal 72 that are indicative of movement of cardiac tissue during atrial contraction, and/or the presence of mechanical perturbations associated with the S4 heart sound. As another example, mechanical sensing module 60 may detect a ventricular contraction based on features in motion signal 72 that are indicative of movement of cardiac tissue during ventricular contraction, and/or the presence of mechanical perturbations associated with the S1 heart sound.

Figure 6:
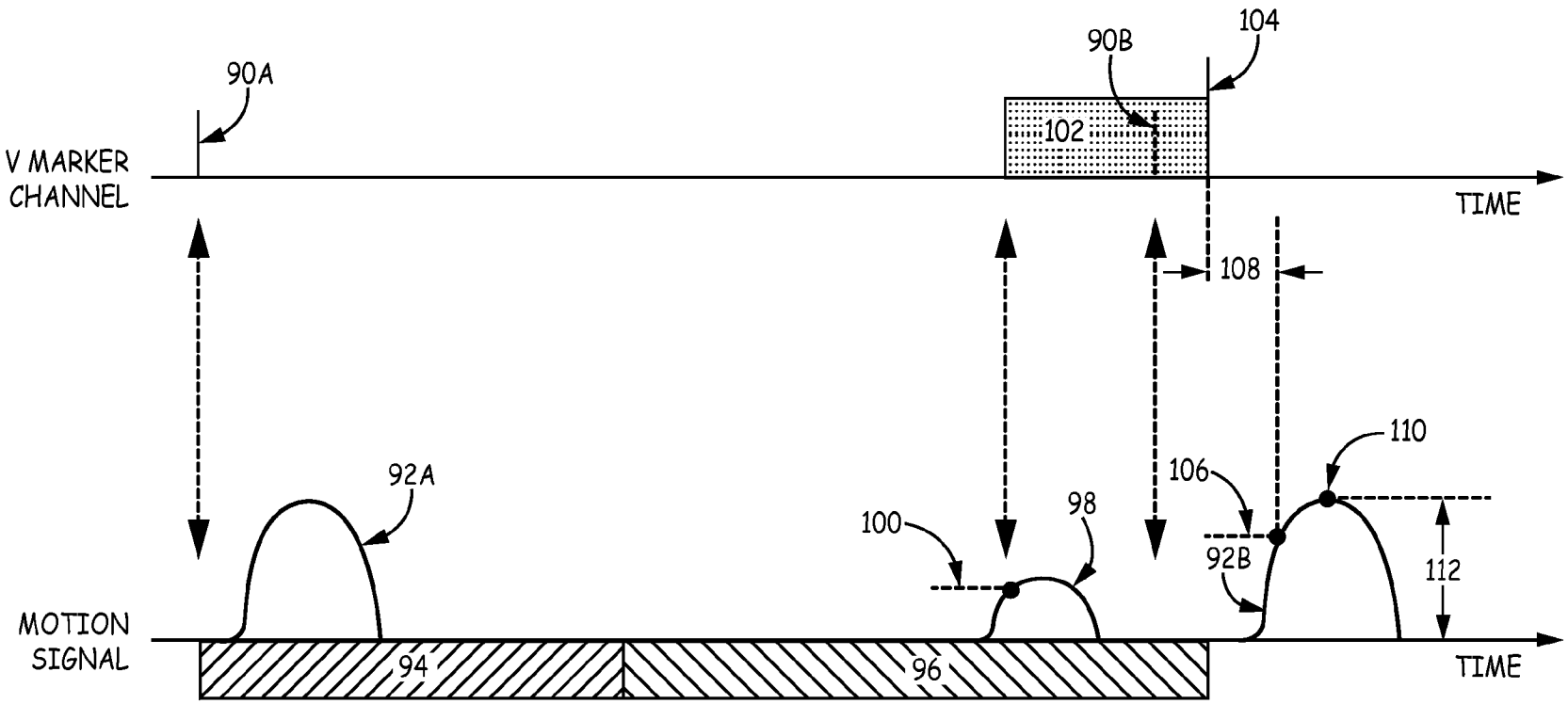
FIG. 6 is a timing diagram illustrating an example technique for delivering atrio-synchronous ventricular pacing based on atrial contraction detection.

FIG. 6 is a timing diagram illustrating an example technique for delivering atrio-synchronous ventricular pacing based on atrial contraction detection. The timing diagram of FIG. 6 includes a ventricular marker channel, and a corresponding motion signal. According to the example technique for delivering atrio-synchronous ventricular pacing based on atrial contraction detection, mechanical sensing module 60 identifies an activation of a ventricle, e.g., right ventricle 18. An activation of a ventricle may be an intrinsic or paced depolarization of the ventricle, or a mechanical contraction of the ventricle. Mechanical sensing module 60 may identify activation of a ventricle by determining that electrical sensing module 56 detected an intrinsic depolarization 90A of the ventricle, by determining that stimulation module 54 delivered a pacing pulse to the ventricle, or by detecting mechanical contraction 92A of ventricle.

In response to identifying activation of the ventricle, mechanical sensing module 60 waits for an atrial contraction detection delay period 94, and then analyzes the motion signal generated by motion sensor 58 within an atrial contraction detection window 96 that begins the atrial contraction detection delay period 94 after the activation of the ventricle, i.e., that begins upon completion of the atrial contraction detection delay period 94. In the example of FIG. 6, mechanical sensing module 60 determined that electrical sensing module detected ventricular depolarization 90A, and analyzes the motion signal within atrial contraction detection window 96 that begins atrial contraction detection delay period 94 after detection of ventricular depolarization 90A.

Starting atrial contraction detection window 96 upon completion of atrial contraction delay period 94 may allow mechanical sensing module 60 to avoid misidentifying ventricular contraction 92A, or other motion of heart during the cardiac cycle prior to atrial depolarization and contraction, as an atrial contraction. In some examples, atrial contraction delay period 94 is at least approximately 300 milliseconds. In some examples, atrial contraction delay period 94 is at least approximately 400 milliseconds, or is approximately 400 milliseconds. In some examples, atrial contraction detection delay period 94 is at least approximately 600 milliseconds. In some examples, processing module 50 and/or mechanical sensing module 60 adjusts atrial contraction detection delay period 94 based on a heart rate of patient 14, e.g., based on one or more intervals between consecutive intrinsic ventricular depolarizations detected by electrical sensing module 56. For example, processing module 50 and/or mechanical sensing module 60 may increase atrial contraction detection delay period 94 as heart rate decreases, and decrease atrial contraction detection delay period 94 as heart rate increases. In some examples, a clinician or other user may program a length of atrial contraction delay period 94, e.g., using programmer 22. The user may select the length of atrial contraction delay period 94 based on individual patient characteristics.

Based on the analysis of the motion signal within atrial contraction detection window 96, mechanical sensing module 60 may detect atrial contraction 98. Mechanical sensing module 60 may extend atrial contraction detection window 96, and the associated analysis of the motion signal, until detection of atrial contraction 98, or until a subsequent intrinsic ventricular depolarization 90B is detected by electrical sensing module 56, or a subsequent ventricular pacing pulse 104 is delivered by stimulation module 54. In some examples, as described above, mechanical sensing module 60 filters the motion signal within atrial contraction detection window 96. Mechanical sensing module 60 may also rectify the motion signal within atrial contraction detection window 96. In some examples, mechanical sensing module 60 detects atrial contraction 98 by comparing an amplitude of the motion signal within atrial contraction detection window 96 to a threshold 100. In some examples, mechanical sensing module 60 determines a derivative signal of the motion signal, e.g., the filtered and/or rectified motion signal, and compares an amplitude of the derivative signal, which represents the rate of change of the motion signal, to threshold 100. In some examples, mechanical sensing module 60 detects the time of atrial contraction 98 as the earliest time point at which the amplitude of the motion signal, or it derivative signal, exceeds threshold 100.

In some examples, threshold 100 is a constant value, which may be determined by a manufacturer of an LPD 12A, or programmed by a clinician using programmer 22. In other examples, mechanical sensing module 60 and/or processing module 50 determines threshold 100 based on a peak amplitude of the motion signal during one or more previously detected atrial contractions. For example, mechanical sensing module 60 and/or processing module 50 may determine that threshold 100 is a value within a range from approximately 20 percent to approximately 80 percent, such as approximately 50 percent, of the peak amplitude of the motion signal during the most recently detected atrial contraction, or of an average peak amplitude of the motion signal during a plurality of previously detected atrial contractions.

In some examples, instead of or in addition to detection of atrial contraction 98 based on a comparison of the motion signal to threshold 100, mechanical sensing module 60 may detect atrial contraction 98 using morphological comparison techniques. For example, mechanical sensing module 60 may compare the motion signal within atrial contraction detection window 96 to one or more templates representing one or more features of a motion signal during atrial contraction. Mechanical sensing module 60 may detect atrial contraction 98 at the point when a statistic resulting from the comparison indicates a sufficient level of similarity between the motion signal and the one or more templates.

In some examples, processing module 50 determines whether electrical sensing module 56 detects an intrinsic ventricular depolarization 90B resulting from the atrial depolarization that led to atrial contraction 98. For example, processing module 50 may determine whether electrical sensing module 56 detects intrinsic ventricular depolarization 90B within an AV interval 102 that begins upon detection of atrial contraction 98 by mechanical sensing module 60. If electrical sensing module 56 does not detect intrinsic depolarization 90B within AV interval 102, e.g., because it did not occur due to AV nodal block, then processing module 50 controls electrical stimulation module 54 to generate and deliver ventricular pacing pulse 104 at the expiration of AV interval 102. In this manner, LPD 12A delivers atrio-synchronous ventricular pacing based on detection of atrial contractions.

Due to the delay between atrial depolarization and atrial contraction 98, and the resulting temporal proximity between atrial contraction 98 and the time at which a paced or intrinsic ventricular depolarization should occur, AV interval 102, which may be referred to as a mechanical AV interval, may be shorter than an (electrical) AV interval employed by a pacemaker that provides atrio-synchronous ventricular pacing based on detection of atrial depolarizations. In some examples, AV interval 102 is less than approximately 100 milliseconds. In some examples, AV interval 102 is less than approximately 50 milliseconds. In some examples, AV interval 102 is approximately 30 milliseconds. In some examples, mechanical AV interval 102 is approximately 20 to 30 milliseconds shorter than an electrical AV interval for the patient.

In some examples, processing module 50 does not employ an AV interval. In such examples, upon detection of atrial contraction 98 by mechanical sensing module 60, processing module determines whether electrical sensing module 56 has detected intrinsic ventricular depolarization 90B. If electrical sensing module 56 has not detected intrinsic ventricular depolarization 90B, then processing module 50 controls stimulation module 54 to generate and deliver a ventricular pacing pulse.

In some examples, LPD 12A determines whether the delivery of ventricular pacing pulse 104 was effective based on detection of the ventricular contraction 92B resulting from the delivery of pacing pulse 104. In such examples, mechanical sensing module 60 detects ventricular contraction 92B based on the motion signal, e.g., based on a comparison of the motion signal to a threshold 106 in a manner similar to that employed for detection of atrial contraction 98 based on threshold 100, or based on a morphological analysis. In some examples, mechanical sensing module 60 detects the time of ventricular contraction 110 to be the first time-point after delivery of pacing pulse 104 when the amplitude of the motion signal exceeds threshold 106. Mechanical sensing module 60 and/or processing module 50 may determine an interval 108 from delivery of pacing pulse 104 to a time of detection of ventricular contraction 92B. Mechanical sensing module 60 may also determine a peak amplitude 110 of the motion signal during ventricular contraction 92B.

In some examples, processing module 50 adjusts AV interval 102 based on the determination of whether the delivery of pacing pulse 104 to the ventricle was effective. For example, processing module 50 may decrease AV interval 102 in response to determining that interval 108 is less than a threshold. Additionally or alternatively, processing module 50 may increase AV interval 102 in response to determining that peak amplitude 110 is greater than a threshold.

Figure 7:
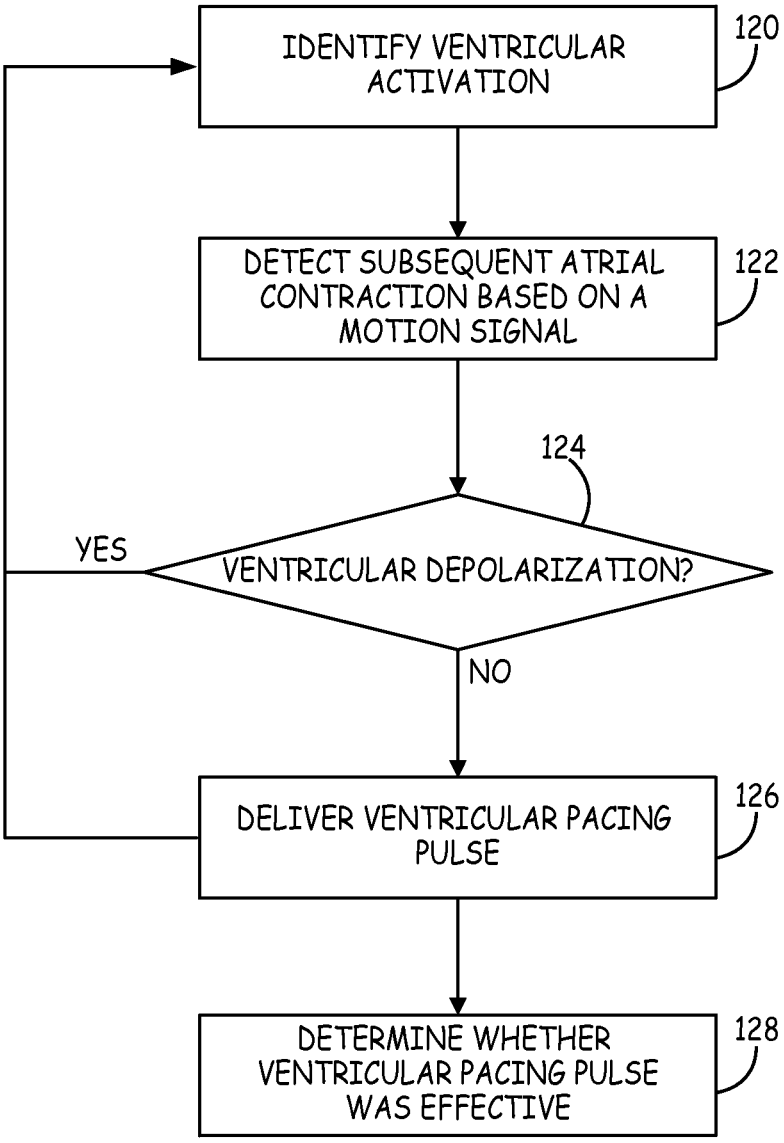
FIG. 7 is a flow diagram of an example technique for delivering atrio-synchronous ventricular pacing based on atrial contraction detection that may be performed by a leadless pacing device implanted within a ventricle.

FIG. 7 is a flow diagram of an example technique for delivering atrio-synchronous ventricular pacing based on atrial contraction detection that may be performed by a LPD implanted within a ventricle, such as LPD 12A or LPD 12B implanted within right ventricle 18 of heart 16. The example technique of FIG. 7 may be performed, at least in part, by a processing module 50 of such an LPD. According to the example technique of FIG. 7, the LPD identifies ventricular activation (120), and detects a subsequent atrial contraction based on a motion signal generated by a motion sensor of the LPD (122). The LPD then determines whether an intrinsic ventricular depolarization resulting from the atrial depolarization that caused the detected atrial contraction has been detected, e.g., within an AV interval beginning upon detection of the atrial contraction (124).

If the LPD detects an intrinsic ventricular depolarization resulting from the atrial depolarization that caused the detected atrial contraction (YES of 124), then the LPD identifies the intrinsic ventricular depolarization as a ventricular activation that begins the next cardiac cycle (120). If the LPD does not detect an intrinsic ventricular depolarization resulting from the atrial depolarization that caused the detected atrial contraction (NO of 124), then the LPD delivers a ventricular pacing pulse (126). For example, the LPD may deliver a ventricular pacing pulse upon expiration of the AV interval without detecting an intrinsic ventricular depolarization. The LPD identifies delivery of the ventricular pacing pulse as a ventricular activation that begins the next cardiac cycle (120). The LPD may also determine whether the delivery of the cardiac pacing pulse was effective, e.g., as described above with respect to FIG. 6 (128).

Figure 8:
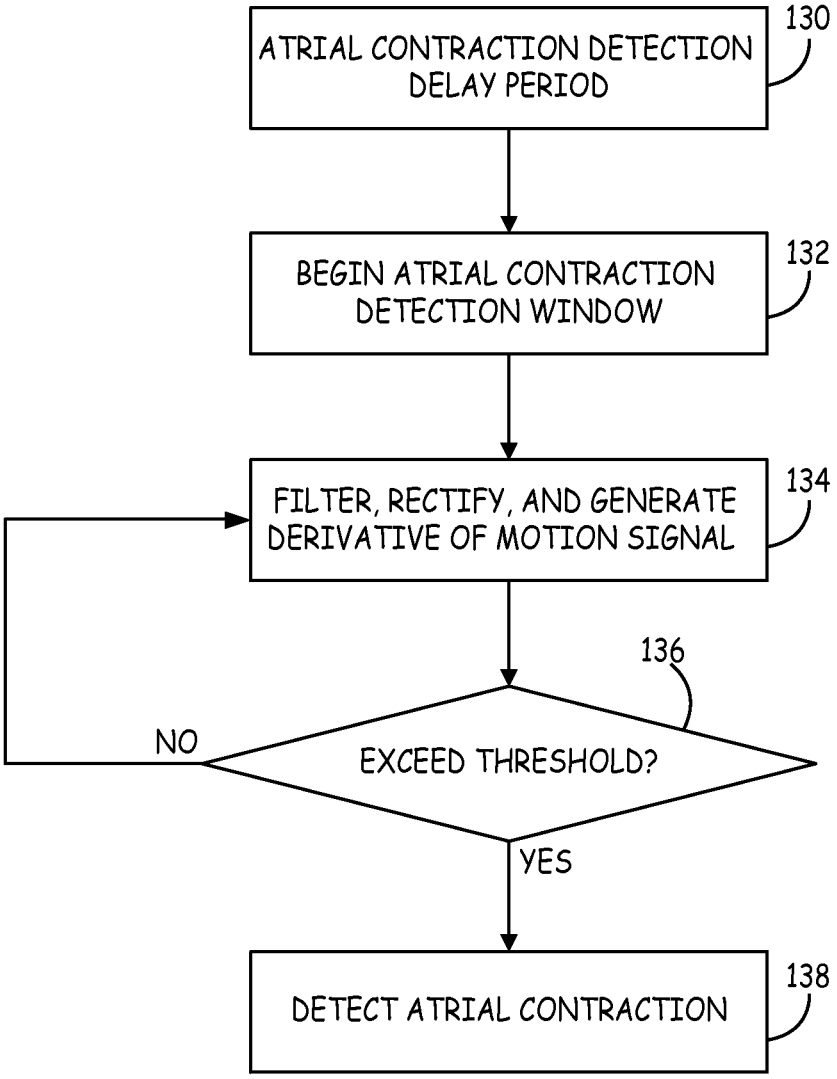
FIG. 8 is a flow diagram illustrating an example technique for detecting an atrial contraction based on analysis of a motion signal that may be performed by a leadless pacing device implanted within a ventricle.

FIG. 8 is a flow diagram illustrating an example technique for detecting an atrial contraction based on analysis of a motion signal (e.g., 122 of FIG. 7) that may be performed by a LPD implanted within a ventricle, such as LPD 12A or LPD 12B implanted within right ventricle 18 of heart 16. The example technique of FIG. 8 may be performed, at least in part, by a processing module 50 of such an LPD. According to the example technique of FIG. 8, the LPD begins an atrial contraction detection delay period upon identification of a ventricular activation event (130). The LPD begins an atrial contraction detection window upon expiration of the atrial contraction delay period (132). The LPD analyzes the motion signal generated by the motion sensor of the LPD within the atrial contraction detection window.

The LPD filters the motion signal within the atrial contraction detection window, rectifies the filtered signal, and generates a derivative signal of the filtered and rectified motion signal within the atrial contraction detection window (134). The LPD determines whether an amplitude of the derivative signal within the atrial contraction detection window exceeds a threshold (136). In response to determining that the amplitude of the derivative signal within the atrial contraction detection window exceeds the threshold (YES of 136), the LPD detects an atrial contraction (138).

Figure 9:
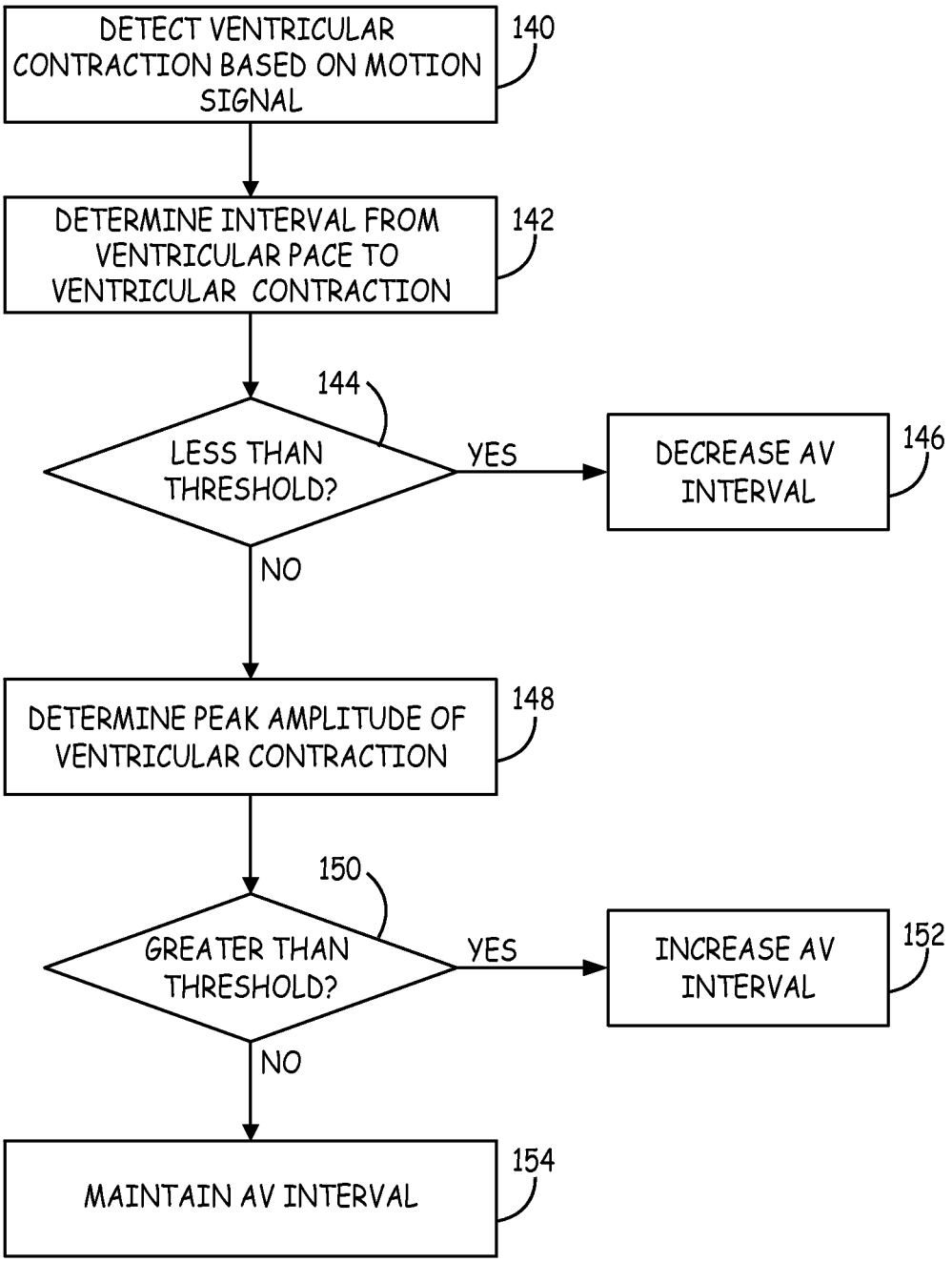
FIG. 9 is a flow diagram illustrating an example technique for verifying efficacy of atrio-synchronous ventricular pacing based on atrial contraction detection that may be performed by a leadless pacing device implanted within a ventricle.

FIG. 9 is a flow diagram illustrating an example technique for verifying efficacy of atrio-synchronous ventricular pacing based on atrial contraction detection that may be performed by a LPD implanted within a ventricle, such as LPD 12A or LPD 12B implanted within right ventricle 18 of heart 16. According to the example technique of FIG. 9, the LPD detects a ventricular contraction resulting from a ventricular pacing pulse based on the motion signal generated by a motion sensor of the LPD after delivery of the ventricular pacing pulse (140). For example, the LPD may detect a time of the ventricular contraction as a time when an amplitude of the motion signal, e.g., an amplitude of a derivative signal generated from a filtered and rectified motion signal, exceeds a threshold.

The LPD determines an interval from the delivery of the ventricular pacing pulse to the time of detection of the ventricular contraction (142). The LPD determines whether the interval is less than a threshold (144). If the interval is less than the threshold (YES of 144), then the LPD decreases an AV interval used for delivery of atrio-synchronous ventricular pacing pulses after detection of an atrial contraction (146).

If the interval is not less than the threshold, e.g., is greater than the threshold (NO of 144), then the LPD determines a peak amplitude of the motion signal during the detected ventricular contraction (148). The LPD determines whether the peak amplitude of the motion signal during the detected ventricular contraction is greater than a threshold (150). If the peak amplitude is greater than the threshold (YES of 150), then the LPD increases an AV interval used for delivery of atrio-synchronous ventricular pacing pulses after detection of an atrial contraction (152). If the peak amplitude is not greater than the threshold, e.g., is less than the threshold (NO of 150), then the LPD maintains the AV interval at its current value (154).

Figure 10:
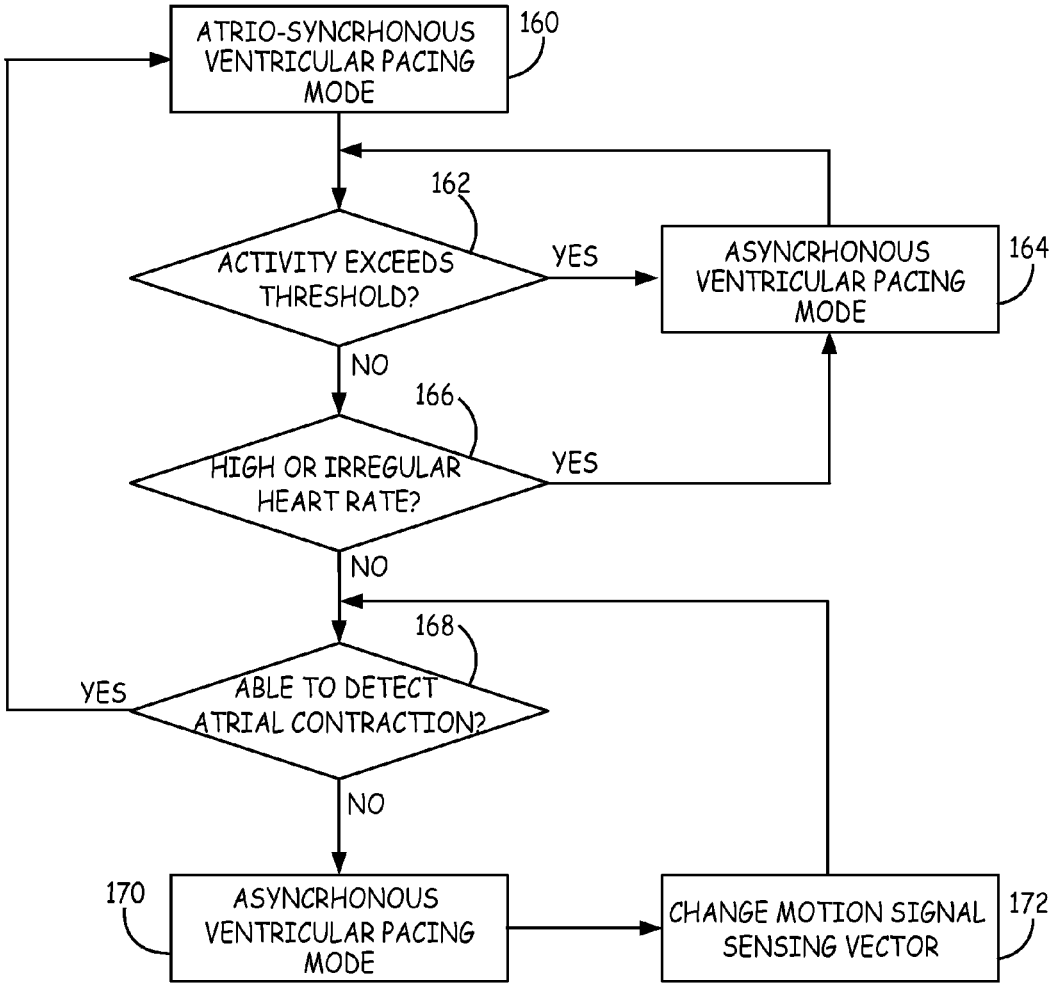
FIG. 10 is a flow diagram illustrating an example technique for switching between an atrio-synchronous ventricular pacing mode and an asynchronous pacing mode that may be performed by a leadless pacing device implanted within a ventricle.

FIG. 10 is a flow diagram illustrating an example technique for switching between an atrio-synchronous ventricular pacing mode and an asynchronous pacing mode that may be performed by a LPD implanted within a ventricle, such as LPD 12A or LPD 12B implanted within right ventricle 18. The example technique of FIG. 10 may be performed, at least in part, by a processing module 50 of such an LPD. According to the example technique of FIG. 10, the LPD operates in an atrio-synchronous ventricular pacing mode in which the LPD delivers atrio-synchronous ventricular pacing based detection of atrial contractions, as described herein (160). The atrio-synchronous ventricular pacing mode in which the LPD delivers atrio-synchronous ventricular pacing based detection of atrial contractions may be similar to a conventional VDD pacing mode, and may be referred to as a VDD pacing mode.

The LPD determines whether a patient activity level, or a level of motion experienced by the patient, exceeds a threshold (162). The LPD may determine the patient activity or motion level based on the motion signal generated by the motion sensor of the LPD. If the activity or motion level exceeds the threshold (YES of 162), then the LPD switches to an asynchronous ventricular pacing mode (164). In the asynchronous ventricular pacing mode, the LDP may deliver pacing pulses to the ventricle if an intrinsic ventricular depolarization is not detected within a VV interval from the last paced or intrinsic ventricular depolarization. The asynchronous ventricular pacing mode of the LPD may be similar to a conventional VVI or VVIR pacing mode, and may be referred to as a WI or VVIR pacing mode.

If the activity or motion level does not exceed the threshold, e.g., is less than the threshold (NO of 162), then the LPD determines whether the heart rate is greater than a threshold, e.g., greater than approximately 80 beats-per-minute or approximately 100 beats-per-minute, and/or irregular (166). The LPD may determine the heart rate and its regularity based on intervals between previous ventricular depolarizations. If the heart rate is greater than the threshold and/or irregular (YES of 166), then the LPD switches to the asynchronous ventricular pacing mode (164).

If the heart rate is not greater than the threshold and/or not irregular (NO of 166), then the LPD determines whether it is able to detect atrial contractions based on an analysis of the motion signal generated by a motion sensor of the LPD (168). For example, the LPD may determine that it is unable to detect atrial contractions if it determines that it has not detected atrial contractions for a predetermined number of cardiac cycles. The predetermined number of cardiac cycles may be any number of one or more cardiac cycles, which may be consecutive or non-consecutive. For example, the predetermined number of cardiac cycles may be three. If LPD determines that it is unable to detect atrial contraction (NO of 168), then the LPD switches to the asynchronous ventricular pacing mode (170). If the LPD determines that it is unable to detect atrial contractions (NO of 168), then the LPD may also change a motion signal sensing vector according to which the LPD derives the motion signal from one or more of a plurality of signals generated by the motion sensor, e.g., the plurality accelerometers of the motion sensor (172).

If the LPD determines that it is able to detect atrial contractions (YES of 168), then LPD may continue to deliver ventricular pacing according to the atrio-synchronous ventricular pacing mode (160). Further, after delivering pacing according to the asynchronous pacing mode (164, 170) for a period of time, or until a condition that led to the switch to the asynchronous mode has abated, the LPD may switch to delivery of ventricular pacing according to the atrio-synchronous ventricular pacing mode.

Figure 11:
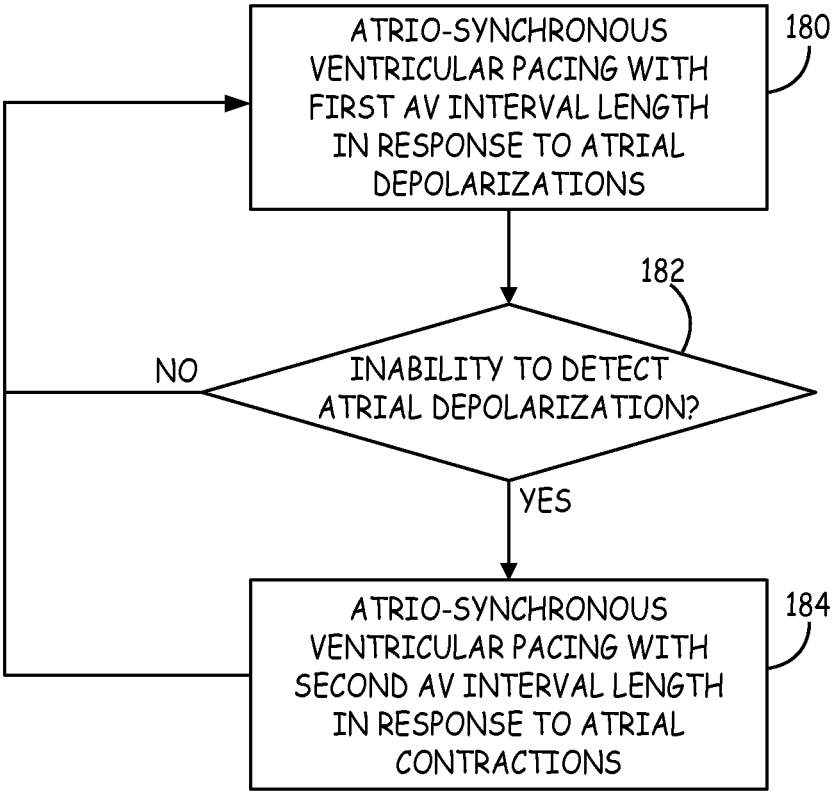
FIG. 11 is a flow diagram illustrating an example technique for switching between atrio-synchronous ventricular pacing in response to atrial depolarizations and atrio-synchronous ventricular pacing in response to atrial contractions that may be performed by a leadless pacing device implanted within a ventricle.

FIG. 11 is a flow diagram illustrating an example technique for switching between atrio-synchronous ventricular pacing in response to atrial depolarizations and atrio-synchronous ventricular pacing in response to atrial contractions that may be performed by a LPD implanted within a ventricle, such as right ventricle 18, that is able to detect depolarizations of an atrium, such as right atrium 20. LPD 12B that is coupled to sensing extension 40 is one example of such an LPD, although LPD 12A may also be configured to detect depolarizations of the atrium. The example technique of FIG. 11 may be performed by a processing module 50 of such an LPD.

According to the example technique of FIG. 11, the LPD delivers atrio-synchronous pacing a first, electrical AV interval after detection of atrial depolarizations (180). The LPD determines whether it is unable to detect atrial depolarizations (182). For example, the LPD may determine that it is unable to detect atrial depolarizations if it determines that it has not detected atrial depolarizations for a predetermined number of cardiac cycles, e.g., has not detected an atrial depolarization between consecutive ventricular depolarizations of a predetermined number of cardiac cycles. The predetermined number of cardiac cycles may be any number of one or more cardiac cycles, which may be consecutive or non-consecutive. If LPD determines that it is unable to detect atrial depolarizations (YES of 182), then the LPD may activate atrial contraction detection, and switch to delivery of atrio-synchronous pacing a second, mechanical AV interval after detection of atrial contractions (184). If LPD determines that it is able to detect atrial depolarizations (NO of 182), or some time delivering atrio-synchronous ventricular pacing based on atrial contraction detection (184), then the LPD may continue or switch back to delivery of atrio-synchronous ventricular pacing based on atrial depolarization detection (180).

The techniques described in this disclosure, including those attributed to LPDs 12, programmer 22, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

What is claimed is:

1. A leadless pacing device configured to deliver atrio-synchronous ventricular pacing, the leadless pacing device comprising:

a plurality of electrodes;

a motion sensor configured to generate a motion signal [as a function of] *based on* movement of a heart of a patient;

[a] stimulation [module] *circuitry* coupled to the plurality of electrodes, wherein the stimulation [module] *circuitry* is configured to generate pacing pulses and deliver the pacing pulses to a ventricle of the heart via the plurality of electrodes;

[an] electrical sensing [module] *circuitry* coupled to the plurality of electrodes, wherein the electrical sensing [module] *circuitry* is configured to detect depolarizations of the ventricle within a cardiac electrogram sensed via the plurality of electrodes;

[a] mechanical sensing [module] *circuitry* coupled to the motion sensor and configured to:

receive the motion signal from the motion sensor;

identify an activation of the ventricle;

[upon] *in response to* identification of the activation of the ventricle, initiate an atrial contraction detection delay period;

analyze the motion signal within an atrial contraction detection window that begins upon completion of the atrial contraction detection delay period; and detect a contraction of an atrium of the heart based on the analysis of the motion signal within the atrial contraction detection window;

[a] processing [module] *circuitry* configured to control the stimulation [module] *circuitry* to generate a pacing pulse and deliver the pacing pulse to the ventricle via the plurality of electrodes in response to the detection of the contraction of the atrium by the mechanical sensing [module] *circuitry*; and a housing configured to be implanted within the ventricle, wherein the housing encloses the motion sensor, the stimulation [module] *circuitry*, the electrical sensing [module] *circuitry*, the mechanical sensing [module] *circuitry*, and the processing [module] *circuitry*;

wherein the processing [module] *circuitry* is configured to:

determine that the electrical sensing [module] *circuitry* did not detect a depolarization of the ventricle within an atrioventricular (AV) interval [beginning] *timed from* when the mechanical sensing [module] *circuitry* detected the contraction of the atrium; and control the stimulation [module] *circuitry* to generate the pacing pulse and deliver the pacing pulse to the ventricle via the plurality of electrodes in response to the determination; and, wherein the mechanical sensing [module] *circuitry* is configured to detect a contraction of the ventricle based on the motion signal after delivery of the pacing pulse to the ventricle, and the processing [module] *circuitry* is configured to[:] determine whether the delivery of the pacing pulse to the ventricle was effective based on the detection of the contraction of the ventricle[; and adjust the AV interval based on the determination of whether the delivery of the pacing pulse to the ventricle was effective].

2. The leadless pacing device of claim 1, wherein the processing [module] *circuitry* is configured to:

determine that an interval from the delivery of the pacing pulse to the detection of the contraction of the ventricle is less than a threshold; and decrease the AV interval in response to the determination that the interval from the delivery of the pacing pulse to the detection of the contraction of the ventricle is less than the threshold.

3. The leadless pacing device of claim 1, wherein the mechanical sensing [module] *circuitry* is configured to:

detect a peak of the [ventricular] contraction *of the ventricle* based on the motion signal; and determine an amplitude of the motion signal at the peak, and wherein the processing [module] *circuitry* is configured to:

determine that the amplitude is greater than the threshold; and increase the AV interval in response to the determination that the amplitude is greater than the threshold.

4. A leadless pacing device configured to deliver atrio-synchronous ventricular pacing, the leadless pacing device comprising:

a plurality of electrodes;

a motion sensor configured to generate a motion signal [as a function of] *based on* movement of a heart of a patient;

[a] stimulation [module] *circuitry* coupled to the plurality of electrodes, wherein the stimulation [module] *circuitry* is configured to generate pacing pulses and deliver the pacing pulses to a ventricle of the heart via the plurality of electrodes;

[an] electrical sensing [module] *circuitry* coupled to the plurality of electrodes, wherein the electrical sensing [module] *circuitry* is configured to detect depolarizations of the ventricle within a cardiac electrogram sensed via the plurality of electrodes, *wherein the electrical sensing circuitry is further configured to detect depolarizations of at least one atrium of the heart*;

[a] mechanical sensing [module] *circuitry* coupled to the motion sensor and configured to:

receive the motion signal from the motion sensor;

identify an activation of the ventricle;

[upon] *in response to* identification of the activation of the ventricle, initiate an atrial contraction detection delay period;

analyze the motion signal within an atrial contraction detection window that begins upon completion of the atrial contraction detection delay period; and detect a contraction of an atrium of the heart based on the analysis of the motion signal within the atrial contraction detection window;

[a] processing [module] *circuitry* configured to control the stimulation [module] *circuitry* to generate [a] *one or more* pacing [pulse] *pulses* and deliver the pacing [pulse] *pulses* to the ventricle via the plurality of electrodes [in response to the detection of the contraction of the atrium by the mechanical sensing module]; and a housing configured to be implanted within the ventricle, wherein the housing encloses the motion sensor, the stimulation [module] *circuitry*, the electrical sensing [module] *circuitry*, the mechanical sensing [module] *circuitry*, and the processing [module] *circuitry*;

[wherein the processing module is configured to:

determine that the electrical sensing module did not detect a depolarization of the ventricle within an atrioventricular (AV) interval beginning when the mechanical sensing module detected the contraction of the atrium; and control the stimulation module to generate the pacing pulse and deliver the pacing pulse to the ventricle via the plurality of electrodes in response to the determination; and, wherein the AV interval comprises a mechanical AV interval, wherein the electrical sensing module is configured to detect depolarizations of the atrium within the cardiac electrogram sensed via the plurality of electrodes,]

wherein, in response to the electrical sensing [module] *circuitry* detecting a depolarization of the atrium, the processing [module] *circuitry* is configured to:

determine that the electrical sensing [module] *circuitry* did not detect a depolarization of the ventricle within an electrical *atrioventricular* (AV) interval [beginning] *timed from* when the electrical sensing [module] *circuitry* detected the depolarization of the atrium; and control the stimulation [module] *circuitry* to generate [a] *one of the* pacing [pulse] *pulses* and deliver the pacing pulse to the ventricle via the plurality of electrodes in response to the determination that the electrical sensing [module] *circuitry* did not detect a depolarization of the ventricle, wherein the processing [module] *circuitry* is further configured to determine that the electrical sensing [module] *circuitry* did not detect a depolarization of the atrium during [a predetermined number of] one or more cardiac cycles and, in response to the determination:

control the mechanical sensing [module] *circuitry* to detect [a] *the* contraction of the atrium based on the motion signal;

determine that the electrical sensing [module] *circuitry* did not detect a depolarization of the ventricle within [the] *a* mechanical AV interval [beginning] *timed from* when the mechanical sensing [module] *circuitry* detected the contraction of the atrium; and control the stimulation [module] *circuitry* to generate [a] *one of the* pacing [pulse] *pulses* and deliver the pacing pulse to the ventricle via the plurality of electrodes in response to the determination that the mechanical sensing [module] *circuitry* did not detect a depolarization of the ventricle, and wherein the electrical AV interval is greater than the mechanical AV interval.

5. A leadless pacing device configured to deliver atrio-synchronous ventricular pacing, the leadless pacing device comprising:

a plurality of electrodes;

a motion sensor configured to generate a motion signal [as a function of] *based on* movement of a heart of a patient;

[a] stimulation [module] *circuitry* coupled to the plurality of electrodes, wherein the stimulation [module] *circuitry* is configured to generate pacing pulses and deliver the pacing pulses to a ventricle of the heart via the plurality of electrodes;

[an] electrical sensing [module] *circuitry* coupled to the plurality of electrodes, wherein the electrical sensing [module] *circuitry* is configured to detect depolarizations of the ventricle within a cardiac electrogram sensed via the plurality of electrodes;

[a] mechanical sensing [module] *circuitry* coupled to the motion sensor and configured to:

receive the motion signal from the motion sensor;

identify an activation of the ventricle;

[upon] *in response to* identification of the activation of the ventricle, initiate an atrial contraction detection delay period;

analyze the motion signal within an atrial contraction detection window that begins upon completion of the atrial contraction detection delay period; and detect a contraction of an atrium of the heart based on the analysis of the motion signal within the atrial contraction detection window;

[a] processing [module] *circuitry* configured to control the stimulation [module] *circuitry* to generate a pacing pulse and deliver the pacing pulse to the ventricle via the plurality of electrodes in response to the detection of the contraction of the atrium by the mechanical sensing [module] *circuitry*; and a housing configured to be implanted within the ventricle, wherein the housing encloses the motion sensor, the stimulation [module] *circuitry*, the electrical sensing [module] *circuitry*, the mechanical sensing [module] *circuitry*, and the processing [module] *circuitry*;

wherein the processing [module] *circuitry* is configured to:

determine a heart rate of the patient based on depolarizations detected by the electrical sensing [module] *circuitry*;

determine that the heart rate exceeds a threshold; and control the stimulation [module] *circuitry* to generate pacing pulses and deliver the pacing pulses to the ventricle according to an asynchronous ventricular pacing mode [in response to] *based on* the determination that the heart rate exceeds the threshold.

6. A leadless pacing device configured to deliver atrio-synchronous ventricular pacing, the leadless pacing device comprising:

a plurality of electrodes;

a motion sensor configured to generate a motion signal [as a function of] *based on* movement of a heart of a patient;

[a] stimulation [module] *circuitry* coupled to the plurality of electrodes, wherein the stimulation [module] *circuitry* is configured to generate pacing pulses and deliver the pacing pulses to a ventricle of the heart via the plurality of electrodes;

[an] electrical sensing [module] *circuitry* coupled to the plurality of electrodes, wherein the electrical sensing [module] *circuitry* is configured to detect depolarizations of the ventricle within a cardiac electrogram sensed via the plurality of electrodes;

[a] mechanical sensing [module] *circuitry* coupled to the motion sensor and configured to:

receive the motion signal from the motion sensor;

identify an activation of the ventricle;

[upon] *in response to* identification of the activation of the ventricle, initiate an atrial contraction detection delay period;

analyze the motion signal within an atrial contraction detection window that begins upon completion of the atrial contraction detection delay period; and detect a contraction of an atrium of the heart based on the analysis of the motion signal within the atrial contraction detection window;

[a] processing [module] *circuitry* configured to control the stimulation [module] *circuitry* to generate a pacing pulse and deliver the pacing pulse to the ventricle via the plurality of electrodes in response to the detection of the contraction of the atrium by the mechanical sensing [module] *circuitry*; and a housing configured to be implanted within the ventricle, wherein the housing encloses the motion sensor, the stimulation [module] *circuitry*, the electrical sensing [module] *circuitry*, the mechanical sensing [module] *circuitry*, and the processing [module] *circuitry*;

wherein the motion sensor comprises a plurality of accelerometers, each of the plurality of accelerometers oriented along a respective axis and configured to generate a respective accelerometer signal, wherein mechanical sensing [module] *circuitry* derives the motion signal based on a first one or more of the accelerometer signals according to a first sensing vector, and wherein the processing [module] *circuitry* is configured to:

determine that the mechanical sensing [module] *circuitry* did not detect a contraction of the atrium during [a predetermined number of] one or more cardiac cycles; and control the mechanical sensing [module] *circuitry* to derive the motion signal based on a second one or more of the accelerometer signals according to a second sensing vector [in response to] *based on* the determination.

7. A method for delivering atrio-synchronous ventricular pacing by a leadless pacing device implanted within a ventricle of a heart of a patient, the method comprising:

identifying an activation of the ventricle;

[upon] *in response to* identification of the activation of the ventricle, initiating an atrial contraction detection delay period;

analyzing a motion signal within an atrial contraction detection window that begins upon completion of the atrial contraction detection delay period, wherein the motion signal is generated by a motion sensor of the leadless pacing device [as a function of] *based on* movement of the heart;

detecting a contraction of an atrium of the heart based on the analysis of the motion signal within the atrial contraction detection window; [and delivering a pacing pulse to the ventricle in response to the detection of the atrial contraction;

determining that a depolarization of the ventricle resulting from the depolarization of the atrium that caused the contraction of the atrium was not detected within an atrioventricular (AV) interval beginning when the contraction of the atrium was detected;

delivering the pacing pulse to the ventricle in response to the determination;]

determining that a depolarization of the ventricle resulting from the depolarization of the atrium that caused the contraction of the atrium was not detected within an atrioventricular (AV) interval [beginning] *timed from* when the contraction of the atrium was detected; [and]

delivering [the] *a* pacing pulse to the ventricle in response to the determination;

detecting a contraction of the ventricle based on the motion signal after delivery of the pacing pulse to the ventricle; *and* determining whether the delivery of the pacing pulse to the ventricle was effective based on the detection of the contraction of the ventricle[; and adjusting the AV interval based on the determination of whether the delivery of the pacing pulse to the ventricle was effective].

8. The method of claim 7, further comprising:

determining that an interval from the delivery of the pacing pulse to the detection of the contraction of the ventricle is less than a threshold; and decreasing the AV interval in response to the determination that the interval from the delivery of the pacing pulse to the detection of the contraction of the ventricle is less than the threshold.

9. The method of claim 7, further comprising:

detecting a peak of the [ventricular] contraction *of the ventricle* based on the motion signal;

determining an amplitude of the motion signal at the peak;

determining that the amplitude is greater than the threshold; and increasing the AV interval in response to the determination that the amplitude is greater than the threshold.

10. A method for delivering atrio-synchronous ventricular pacing by a leadless pacing device implanted within a ventricle of a heart of a patient, the method comprising:

[identifying an activation of the ventricle;

upon identification of the activation of the ventricle, initiating an atrial contraction detection delay period;

analyzing a motion signal within an atrial contraction detection window that begins upon completion of the atrial contraction detection delay period, wherein the motion signal is generated by a motion sensor of the leadless pacing device as a function of movement of the heart;

detecting a contraction of an atrium of the heart based on the analysis of the motion signal within the atrial contraction detection window; and delivering a pacing pulse to the ventricle in response to the detection of the atrial contraction;

determining that a depolarization of the ventricle resulting from the depolarization of the atrium that caused the contraction of the atrium was not detected within an atrioventricular (AV) interval beginning when the contraction of the atrium was detected;

delivering the pacing pulse to the ventricle in response to the determination;

determining that a depolarization of the ventricle resulting from the depolarization of the atrium that caused the contraction of the atrium was not detected within an atrioventricular (AV) interval beginning when the contraction of the atrium was detected; and delivering the pacing pulse to the ventricle in response to the determination;

wherein the leadless pacing device is configured to detect depolarizations of the atrium, and the AV interval comprises a mechanical AV interval, the method further comprising:]

in response to detecting a depolarization of [the] *an* atrium *of the heart*:

determining that a depolarization of the ventricle was not detected within an electrical *atrioventricular* (AV) interval [beginning when the electrical sensing module detected] *timed from the detection of* the depolarization of the atrium; and delivering a pacing pulse to the ventricle in response to the determination that a depolarization of the ventricle was not detected, and in response to determining that a depolarization of the atrium was not detected during [a predetermined number of] one or more cardiac cycles:

detecting a contraction of the atrium based on [the] *a* motion signal;

determining that a depolarization of the ventricle was not detected within [the] *a* mechanical AV interval [beginning] *timed from* when the contraction of the atrium was detected; and delivering a pacing pulse to the ventricle in response to the determination that a depolarization of the ventricle was not detected, and wherein the electrical AV interval is greater than the mechanical AV interval*, and*

*wherein detecting the contraction of the atrium based on the motion signal comprises:*

*identifying an activation of the ventricle;*

*in response to identification of the activation of the ventricle, initiating an atrial contraction detection delay period;*

*analyzing a motion signal within an atrial contraction detection window that begins upon completion of the atrial contraction detection delay period, wherein the motion signal is generated by a motion sensor of the pacing device based on movement of the heart; and*

*detecting the contraction of the based on the analysis of the motion signal within the atrial contraction detection window.*

11. A method for delivering atrio-synchronous ventricular pacing by a leadless pacing device implanted within a ventricle of a heart of a patient, the method comprising:

identifying an activation of the ventricle;

[upon] *in response to* identification of the activation of the ventricle, initiating an atrial contraction detection delay period;

analyzing a motion signal within an atrial contraction detection window that begins upon completion of the atrial contraction detection delay period, wherein the motion signal is generated by a motion sensor of the leadless pacing device [as a function of] *based on* movement of the heart;

detecting a contraction of an atrium of the heart based on the analysis of the motion signal within the atrial contraction detection window; and delivering a pacing pulse to the ventricle in response to the detection of the atrial contraction[;]*, wherein the motion signal is further generated by the motion sensor based on motion of the patient, the method further comprising:* determining an amount of motion of the patient based on the motion signal; and delivering the pacing pulses to the ventricle according to an asynchronous ventricular pacing mode [in response to] *based on* the amount of motion of the patient exceeding a threshold.

12. A method for delivering atrio-synchronous ventricular pacing by a leadless pacing device implanted within a ventricle of a heart of a patient, the method comprising:

identifying an activation of the ventricle;

[upon] *in response to* identification of the activation of the ventricle, initiating an atrial contraction detection delay period;

analyzing a motion signal within an atrial contraction detection window that begins upon completion of the atrial contraction detection delay period, wherein the motion signal is generated by a motion sensor of the leadless pacing device [as a function of] *based on* movement of the heart;

detecting a contraction of an atrium of the heart based on the analysis of the motion signal within the atrial contraction detection window; and delivering a pacing pulse to the ventricle in response to the detection of the atrial contraction[;]*, the method further comprising:* determining a contraction of the atrium was not detected during [a predetermined number of] one or more cardiac cycles; and delivering pacing pulses to the ventricle according to an asynchronous ventricular pacing mode [in response to] *based on* the determination.

13. A method for delivering atrio-synchronous ventricular pacing by a leadless pacing device implanted within a ventricle of a heart of a patient, the method comprising:

identifying an activation of the ventricle;

[upon] *in response to* identification of the activation of the ventricle, initiating an atrial contraction detection delay period;

analyzing a motion signal within an atrial contraction detection window that begins upon completion of the atrial contraction detection delay period, wherein the motion signal is generated by a motion sensor of the leadless pacing device [as a function of] *based on* movement of the heart;

detecting a contraction of an atrium of the heart based on the analysis of the motion signal within the atrial contraction detection window; and delivering a pacing pulse to the ventricle in response to the detection of the atrial contraction[;]*, the method further comprising:* determining that a heart rate *of the heart* exceeds a threshold; and delivering [the] *one or more additional* pacing pulses to the ventricle according to an asynchronous ventricular pacing mode [in response to] *based on* the determination that the heart rate exceeds the threshold.

*14. The leadless pacing device of claim 1, wherein the AV interval begins when the mechanical sensing circuitry detected the contraction of the atrium.*

*15. The leadless pacing device of claim 1, wherein the processing circuitry is configured to adjust the AV interval based on the determination of whether the delivery of the pacing pulse to the ventricle was effective.*

*16. The leadless pacing device of claim 4, wherein the electrical sensing circuitry is configured to detect the depolarizations of the at least one atrium via the plurality of electrodes.*

*17. The leadless pacing device of claim 4, wherein the processing circuitry is configured to control the mechanical sensing circuitry to detect the contraction of the atrium based on the motion signal in response to determining that the electrical sensing circuitry did not detect a depolarization of the atrium during a predetermined number of one or more cardiac cycles.*

*18. The method of claim 7, further comprising adjusting the AV interval based on the determination of whether the delivery of the pacing pulse to the ventricle was effective.*

*19. The method claim 10, wherein detecting the contraction of the atrium based on the motion signal comprises detecting the contraction of the atrium in response to*

*determining that the depolarization of the atrium was not detected during a predetermined number of one or more cardiac cycles.*

*20. The method of claim 12, wherein determining the contraction of the atrium was not detected during one or more cardiac cycles comprises determining the contraction of the atrium was not detected during a predetermined number of one or more cardiac cycles.*

*21. A leadless pacing device configured to deliver atrio-synchronous ventricular pacing, the leadless pacing device comprising:*

*a plurality of electrodes;*

*a motion sensor configured to generate a motion signal based on movement of a heart of a patient;*

*stimulation circuitry coupled to the plurality of electrodes, wherein the stimulation circuitry is configured to generate pacing pulses and deliver the pacing pulses to a ventricle of the heart via the plurality of electrodes;*

*electrical sensing circuitry coupled to the plurality of electrodes, wherein the electrical sensing circuitry is configured to detect depolarizations of the ventricle within a cardiac electrogram sensed via the plurality of electrodes;*

*mechanical sensing circuitry coupled to the motion sensor and configured to:*

*receive the motion signal from the motion sensor;*

*identify an activation of the ventricle;*

*in response to identification of the activation of the ventricle, initiate an atrial contraction detection delay period;*

*analyze the motion signal within an atrial contraction detection window that begins upon completion of the atrial contraction detection delay period; and*

*detect a contraction of an atrium of the heart based on the analysis of the motion signal within the atrial contraction detection window;*

*processing circuitry configured to:*

*determine that the electrical sensing circuitry did not detect a depolarization of the ventricle within an atrioventricular (AV) interval timed from when the mechanical sensing circuitry detected the contraction of the atrium; and*

*control the stimulation circuitry to generate a pacing pulse and deliver the pacing pulse to the ventricle via the plurality of electrodes in response to the determination; and*

*a housing configured to be implanted within the ventricle, wherein the housing encloses the motion sensor, the stimulation circuitry, the electrical sensing circuitry, the mechanical sensing circuitry, and the processing circuitry;*

*wherein the processing circuitry is further configured to:*

*determine a heart rate of the heart; and*

*adjust the atrial contraction detection delay period based on the determined heart rate.*

*22. A leadless pacing device configured to deliver atrio-synchronous ventricular pacing, the leadless pacing device comprising:*

*a plurality of electrodes;*

*a motion sensor configured to generate a motion signal based on movement of a heart of a patient;*

*stimulation circuitry coupled to the plurality of electrodes, wherein the stimulation circuitry is configured to generate pacing pulses and deliver the pacing pulses to a ventricle of the heart via the plurality of electrodes;*

*electrical sensing circuitry coupled to the plurality of electrodes, wherein the electrical sensing circuitry is configured to detect depolarizations of the ventricle within a cardiac electrogram sensed via the plurality of electrodes;*

*mechanical sensing circuitry coupled to the motion sensor and configured to:*

*receive the motion signal from the motion sensor;*

*identify an activation of the ventricle;*

*in response to identification of the activation of the ventricle, initiate an atrial contraction detection delay period;*

*analyze the motion signal within an atrial contraction detection window that begins upon completion of the atrial contraction detection delay period; and*

*detect a contraction of an atrium of the heart based on the analysis of the motion signal within the atrial contraction detection window;*

*processing circuitry configured to:*

*determine that the electrical sensing circuitry did not detect a depolarization of the ventricle within an atrioventricular (AV) interval timed from when the mechanical sensing circuitry detected the contraction of the atrium; and*

*control the stimulation circuitry to generate a pacing pulse and deliver the pacing pulse to the ventricle via the plurality of electrodes in response to the determination; and*

*a housing configured to be implanted within the ventricle, wherein the housing encloses the motion sensor, the stimulation circuitry, the electrical sensing circuitry, the mechanical sensing circuitry, and the processing circuitry;*

*wherein the processing circuitry is further configured to:*

*identify a condition inconsistent with atrio-synchronous ventricular pacing; and*

*control the stimulation circuitry to deliver one or more additional pacing pulses to the ventricle according to an asynchronous ventricular pacing mode based on the identification of the condition.*

*23. The leadless pacing device of claim 22, wherein the motion sensor is configured to generate the motion signal based on motion of the patient and, to identify the condition inconsistent with atrio-synchronous ventricular pacing, the processing circuitry is configured to determine, based on the motion signal, that an amount of motion of the patient satisfies a threshold.*

*24. The leadless pacing device of claim 22, wherein, to identify the condition inconsistent with atrio-synchronous ventricular pacing, the processing circuitry is configured to determine that a contraction of the atrium was not detected during one or more cardiac cycles.*

*25. The leadless pacing device of claim 22, wherein, to identify the condition inconsistent with atrio-synchronous ventricular pacing, the processing circuitry is configured to determine that a heart rate of the heart satisfies a threshold.*

*26. The leadless pacing device of claim 22, wherein, to identify the condition inconsistent with atrio-synchronous ventricular pacing, the processing circuitry is configured to determine that a heart rate irregularity of the heart satisfies a threshold.*

* * * * *